(12) United States Patent
Conjeevaram et al.

(10) Patent No.: US 10,117,843 B2
(45) Date of Patent: Nov. 6, 2018

(54) LEVODOPA AND CARBIDOPA INTESTINAL GEL AND METHODS OF USE

(71) Applicant: AbbVie, Inc., North Chicago, IL (US)

(72) Inventors: Rajkumar Conjeevaram, Lake Bluff, IL (US); Alexandru Deac, Skokie, IL (US); Ye Huang, Gurnee, IL (US); Sean E. Mackey, Grayslake, IL (US); Randy A. Menges, Lake Villa, IL (US); Jayne Zimmerman, Deerfield, IL (US)

(73) Assignee: ABBVIE INC., North Chicago, IL (US)

(*) Notice: Subject to any disclaimer, the term of this patent is extended or adjusted under 35 U.S.C. 154(b) by 0 days.

(21) Appl. No.: 15/001,392

(22) Filed: Jan. 20, 2016

(65) Prior Publication Data

US 2016/0206584 A1    Jul. 21, 2016

Related U.S. Application Data

(60) Provisional application No. 62/272,922, filed on Dec. 30, 2015, provisional application No. 62/105,565, filed on Jan. 20, 2015.

(51) Int. Cl.

| | | |
|---|---|---|
| *A61K 31/198* | (2006.01) | |
| *A61K 45/06* | (2006.01) | |
| *A61K 9/00* | (2006.01) | |
| *A61K 47/32* | (2006.01) | |
| *A61K 47/38* | (2006.01) | |
| *A61K 9/10* | (2006.01) | |
| *A61K 47/10* | (2017.01) | |

(52) U.S. Cl.
CPC .......... *A61K 31/198* (2013.01); *A61K 9/0019* (2013.01); *A61K 9/0053* (2013.01); *A61K 9/10* (2013.01); *A61K 45/06* (2013.01); *A61K 47/10* (2013.01); *A61K 47/32* (2013.01); *A61K 47/38* (2013.01)

(58) Field of Classification Search
CPC .. A61K 31/198; A61K 2300/00; A61K 45/06; A61K 47/10; A61K 47/32; A61K 47/38; A61K 9/0019; A61K 9/0053; A61K 9/10
See application file for complete search history.

(56) References Cited

U.S. PATENT DOCUMENTS

| 3,132,171 A | 5/1964 | Herman Plaut |
| 4,618,484 A | 10/1986 | Pawelek |
| 5,073,547 A | 12/1991 | Casagrande et al. |
| 5,438,047 A | 8/1995 | Santangelo et al. |
| 5,635,213 A | 6/1997 | Nystrom et al. |
| 6,365,180 B1 | 4/2002 | Meyer et al. |
| 8,048,926 B2 | 11/2011 | Atlas |
| 2012/0288446 A1 | 11/2012 | Garigapati et al. |
| 2013/0253056 A1 | 9/2013 | Nemas et al. |
| 2016/0022573 A1 | 1/2016 | Yacoby-Zeevi |

FOREIGN PATENT DOCUMENTS

| EP | 0393781 A2 | 10/1990 |
| WO | WO-94/12153 A1 | 6/1994 |
| WO | WO-2007/138086 A1 | 12/2007 |
| WO | WO-2010/134074 A1 | 11/2010 |
| WO | WO-2011/056240 A2 | 5/2011 |
| WO | WO-2012/066538 A1 | 5/2012 |
| WO | WO-2012/079072 A2 | 6/2012 |
| WO | WO-2013/033453 A2 | 3/2013 |
| WO | WO-2015/069773 A1 | 5/2015 |

OTHER PUBLICATIONS

U.S. Appl. No. 14/919,418, Cardinal-David et al.
Agin, P., et al. (1987), "Phosphorylated Mixed Isomers of L-Dopa Increase Melanin Content in Skins of Skh-2 Pigmented Hairless Mice", *Pigment Cell Research*, 1: 137-142.
Dhareshwar, S., et al. (2008), Your Prodrug Releases Formaldehyde: Should You Be Concerned? No!, *Journal of Pharmaceutical Sciences*, 97(10): 4184-4193.
Hideko Maeda et al. (2011), "Phosphonylation of L-Dopa with Sodium Diphosphonate in Aqueous Solution", *Phosphorus Research Bulletin*, vol. 25, 2011, pp. 56-60.
International Search Report dated Feb. 9, 2016 issued in PCT Patent Application No. PCT/US2015/056686.
Kearney, A., et al. (1992), "The in vitro Enzymic Labilities of Chemically Distinct Phosphomonoester Prodrugs", *Pharmaceutical Research*, 9(4): 497-503.
Pawelek, J., et al. (1986), "Increase in Melanin Formation and Promotion of Cytotoxicity in Cultured Melanoma Cells Caused by Phosphorylated Isomers of I-Dopa", *Cancer Res*, 46: 493-497.
Safadi, M., et al. (1993), "Phosphoryloxymethyl Carbamates and Carbonates—Novel Water-Soluble Prodrugs for Amines and Hindered Alcohols", *Pharmaceutical Research*, 10(9): 1350-1355.
Zhu, Z., et al. (2000), "Phosphate Prodrugs of PD154075", *Bioorganic & Medicinal Chemistry Letters*, 10: 1121-1124.
International Search Report and Written Opinion dated Apr. 11, 2016 issued in PCT/US2016/014005.

*Primary Examiner* — Snigdha Maewall
(74) *Attorney, Agent, or Firm* — Sterne, Kessler, Goldstein & Fox P.L.L.C.

(57) ABSTRACT

The present disclosure relates to (a) an improved pharmaceutical composition comprising a levodopa active agent and a carbidopa active agent (b) methods of producing the pharmaceutical composition and (c) methods of treating Parkinson's disease and associated conditions comprising administering the pharmaceutical composition to a subject with Parkinson's disease.

11 Claims, 11 Drawing Sheets

LEVODOPA AND CARBIDOPA INTESTINAL GEL AND METHODS OF USE

PRIORITY STATEMENT

This United States patent application claims the benefit of U.S. Provisional application 62/105,565 filed 20 Jan. 2015 and 62/272,922 filed 30 Dec. 2015. The entire contents of each patent application recited herein are hereby incorporated by reference.

FIELD OF THE INVENTION

The present disclosure relates to (a) an improved pharmaceutical composition comprising levodopa and carbidopa and (b) methods of treating Parkinson's disease and associated conditions comprising administering the pharmaceutical composition to a subject with Parkinson's disease.

BACKGROUND OF THE INVENTION

Parkinson's disease is a chronic and progressive neurodegenerative condition characterized by reduced levels in the brain of the neurotransmitter dopamine (i.e., 3,4-dihydroxyphenethylamine). Administration of L-dopa currently is the most effective therapy for treating a patient with Parkinson's disease. L-dopa, which unlike dopamine can cross the blood-brain barrier, is enzymatically converted in the brain to dopamine resulting in an increase in dopamine levels:

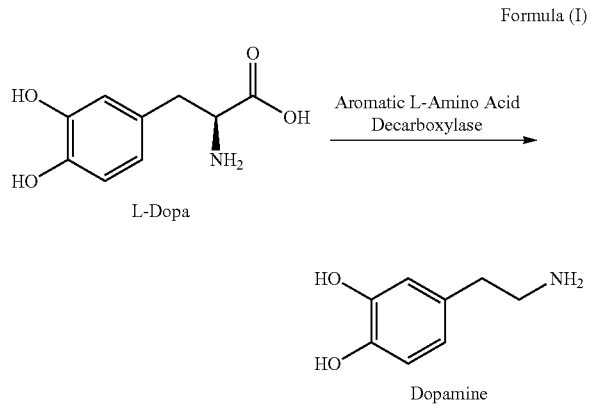

Formula (I)

The conversion of L-dopa to dopamine is catalyzed by aromatic L-amino acid decarboxylase, a ubiquitous enzyme that promotes central as well as peripheral metabolism of L-dopa to dopamine. A relatively large dose of L-dopa is required to achieve therapeutically effective dopamine levels in the brain. Administration of such large L-dopa doses results in elevated peripheral dopamine levels that can cause nausea in some patients. To overcome these problems, L-dopa generally is co-administered with a peripheral aromatic L-amino acid decarboxylase inhibitor such as carbidopa (i.e., (2S)-3-(3,4-dihydroxy-phenyl)-2-hydrazino-2-methylpropanoic acid):

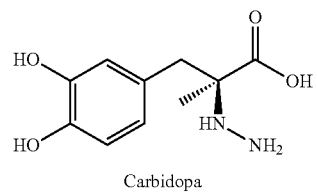

Formula (II)

Co-administration of carbidopa with L-dopa inhibits the peripheral metabolism of L-dopa to dopamine, which significantly reduces the L-dopa dose required for a therapeutically effective response and reduces the associated side effects.

Even when L-dopa and carbidopa are co-administered, however, it is difficult to consistently maintain the desired dopamine levels in the brain due to the relatively short half-life of L-dopa in plasma. In addition, the tolerance of many patients to variability in dopamine levels in the brain decreases as the disease progresses. One approach that has been effective in reducing variability of dopamine levels is the continuous intestinal delivery of an adjustable dose of an L-dopa/carbidopa gel known by its commercial name, DuoDopa®. DuoDopa® is a suspension of L-dopa/carbidopa monohydrate (4:1 ratio of L-dopa to carbidopa monohydrate) in an aqueous gel. The gel is delivered to the proximal small intestine through a jejunal tube inserted through a percutaneous endoscopic gastrostomy port. DuoDopa® is packaged in disposable drug reservoirs ("DDRs") and continuously administered via a software-controlled ambulatory infusion pump. Although L-dopa and carbidopa have been co-administered to treat Parkinson's disease for several decades, a pharmaceutical composition suitable for use in a newer generation of lighter, smaller infusion pumps that deliver gel compositions to the intestine is not currently commercially available.

The current composition of the DuoDopa® L-dopa/carbidopa intestinal gel is a gel for continuous intestinal administration. For long-term administration, the gel is administered with a portable pump directly into the duodenum or upper jejunum via a percutaneous endoscopic gastrostomy tube with an inner intestinal/jejunal tube. Each 1 ml of Duodopa® contains 20 mg levodopa and 5 mg carbidopa monohydrate. Despite the current commercial success of DuoDopa®, the product is subject to limitations in product preparation, including (1) risk of sedimentation of drug particles during storage and administration, (2) chemical instability of carbidopa, which leads to hydrazine formation.

Accordingly, there is a continuing need for improved formulations and methods that can provide continuous and consistent dopamine levels in the brain to effectively treat movement disorders such as Parkinson's disease. The present disclosure provides such improved formulations and methods.

SUMMARY OF THE INVENTION

In one aspect, the present disclosure relates to a pharmaceutical composition comprising a levodopa active agent and a carbidopa active agent for intraduodenal administration wherein the levodopa active agent is provided in an amount of about 4 weight/weight percent (w/w %) of the composition and carbidopa (e.g., carbidopa monohydrate) is provided in an amount of about 1 weight/weight percent of the composition wherein the levodopa and carbidopa are suspended in an aqueous carrier. The pharmaceutical composition has a desired viscosity suitable for storage under refrigerated conditions and/or delivery (e.g., delivered via a pump) at room temperature (e.g., ~20° C. to ~25° C.).

In another aspect, the present disclosure relates to a method of treating Parkinson's disease in a patient in need thereof, wherein the method comprises administering to the patient a pharmaceutical composition comprising a levodopa active agent and a carbidopa active agent for intraduodenal administration wherein the levodopa active agent and carbidopa active agent (e.g., carbidopa monohydrate) are provided in an amount of from about 4 weight/weight percent and 1 weight/weight percent of the composition, respectively, suspended in an aqueous carrier. The pharmaceutical composition has a desired viscosity suitable for storage under refrigerated conditions and/or delivery (e.g., delivered via a pump) at room temperature (e.g., ~20° C. to ~25° C.).

In another aspect, the present disclosure relates to methods of manufacturing a pharmaceutical composition of the invention, in particular a high concentration pharmaceutical composition as disclosed, for example, in Example 1 and FIG. 1 below.

These and additional embodiments of the invention are further described herein.

Further benefits of the present disclosure will be apparent to one skilled in the art from reading this patent application. The embodiments of the disclosure described in the following paragraphs are intended to illustrate the invention and should not be deemed to narrow the scope of the invention.

DETAILED DESCRIPTION OF THE INVENTION

Figure 1:
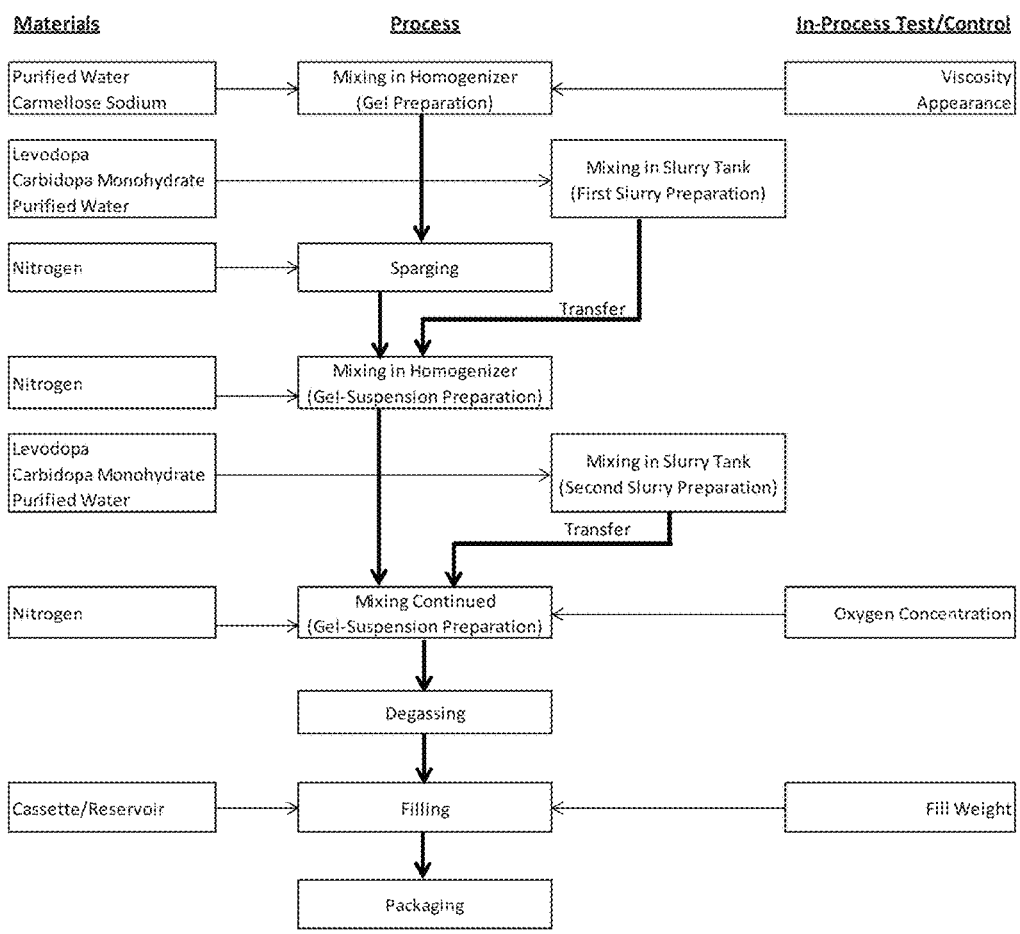
FIG. 1 is a manufacturing process flowchart for producing an exemplary pharmaceutical formulation of the invention.

This written description uses examples to disclose the invention, including the best mode, and also to enable any person skilled in the art to practice the invention, including making and using any of the disclosed pharmaceutical compositions, kits, pharmaceutical dosage forms, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. Definitions

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an," and "the" include plural referents unless the context clearly dictates otherwise.

The term "and/or" as used in a phrase such as "A and/or B" herein is intended to include "A and B", "A or B", "A", and "B".

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The terms "improve" and "improving" have their plain and ordinary meaning to one skilled in the art of pharmaceutical or medical sciences and specifically include ameliorating the effects of Parkinson's disease, or decreasing or lessening a symptom or side effect of Parkinson's disease.

The term "patient" includes mammals and humans, particularly humans.

The term "pharmaceutically acceptable carrier" or "pharmaceutically acceptable excipient" refers to any and all solvents, dispersion media, preservatives, antioxidants, coatings, isotonic and absorption delaying agents, and the like, that are compatible with pharmaceutical administration. The term "aqueous carrier" refers to a pharmaceutically acceptable carrier in which the solvent is water.

The term "pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxy-ethanesulfonic acid, benzenesulfonic acid, 4-chlorobenze-nesulfonic acid, 2-naphthalenesulfonic acid, 4-toluenesulfo-nic acid, camphorsulfonic acid, 4-methyl-bicyclo[2.2.2]-oct-2-ene-1-carboxylic acid, glucoheptonic acid, 3-phenylpropionic acid, trimethylacetic acid, tertiary buty-lacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, trietha-nolamine, N-methylglucamine, dicyclohexylamine, and the like.

The terms "reduce" and "reducing" have their plain and ordinary meanings to one skilled in the art of pharmaceutical or medical sciences and specifically include diminishing or decreasing the number of occurrences, the duration, or the intensity, of a Parkinson's disease symptom or side effect, such as dyskinesias or hallucinations.

The term "therapeutically effective amount" means an amount of a compound that, when administered to a patient suffering from or susceptible to Parkinson's disease or an associated condition is sufficient, either alone or in combination with additional therapies, to effect treatment for Parkinson's disease or the associated condition. The "therapeutically effective amount" will vary depending, for example, on the compound, pharmaceutical composition or pharmaceutical dosage form, the condition treated and its severity, and the age and weight of the patient to be treated.

The terms "treat" and "treating" have their plain and ordinary meaning to one skilled in the art of pharmaceutical or medical sciences and specifically include improving the quality of life or reducing the symptoms or side effects of Parkinson's disease.

II. Pharmaceutical Compositions

The present disclosure relates to a pharmaceutical composition comprising a levodopa active agent and a carbidopa active agent for intraduodenal administration wherein the levodopa active agent and carbidopa active agent are present in a therapeutically effective amount suspended in an aqueous carrier, characterized in that the levodopa active agent and the carbidopa active agent in the carrier has a high shear viscosity of no more than about 4500 cps at room temperature (e.g., ~20° C. to ~25° C., such as ~22° C.) and a low shear viscosity of no less than about 45000 cps under refrigerated storage conditions (for example, at about 2° C. to about 8° C., such as 5° C.). Additionally or alternatively, the pharmaceutical composition—i.e., the aqueous carrier with the levodopa active agent and carbidopa active agent suspended therein—can have a ratio of low shear viscosity to high shear viscosity of not less than about 10. In particular, the aqueous carrier with the levodopa active agent and carbidopa active agent suspended therein can have a high shear viscosity of no more than about 4500 cps at room temperature (e.g., ~20° C. to ~25° C., such as ~22° C.) and a low shear viscosity of no less than about 45000 cps under refrigerated storage conditions (for example, at about 2° C. to about 8° C., such as 5° C.) and a ratio of low shear viscosity to high shear viscosity of not less than about 10. The pharmaceutical compositions may have the aforementioned low shear viscosity and high shear viscosity throughout shelf life. As used herein, "shelf life" includes at least about 2 weeks, for example, at least about 5 weeks, at least about 10 weeks, at least about 15 weeks, or at least about 20 weeks. For example, the pharmaceutical composition can have a high shear viscosity of about 4300-4400 cps (at ~22° C.) and a low shear viscosity of about 49600 cps (at ~5° C.) throughout its shelf life.

Both low shear and high shear viscosity can be measured by routine methods known in the art. For purposes of measuring viscosity of the compositions and formulations disclosed herein, low shear viscosity should be measured in a sample of ~9 mL at a temperature of ~5° C. and a shear rate of ~0.1 sec$^{-1}$. If the viscosity is measured in, e.g., a BROOKFIELD Model LV viscometer (for example in sample chamber SC4-13R with temperature probe and water jacket assembly SC4-45Y), then the test should be conducted with an SC4-31 model spindle. Where other equipment is used, a spindle of corresponding dimensions and specifications can be substituted accordingly.

High sheer viscosity should be measured in a sample of ~16 mL at a temperature of ~22° C. and a shear rate of ~24.1 sec$^{-1}$. If the viscosity is measured in, e.g., a BOHLIN model 88 BV rotational viscometer, then the test should be conducted with a C25 cylinder/spindle system. Where other equipment is used, a spindle of corresponding dimensions and specifications can be substituted accordingly.

In various aspects, the therapeutically effective amount of a levodopa active agent and a carbidopa active agent (e.g., carbidopa monohydrate) present in the pharmaceutical composition may be about 4.0 and 1.0 weight/weight percent of the composition, respectively.

As previously noted, the inherently low aqueous solubility of L-dopa and carbidopa at physiologically acceptable pH for infusion presents a significant technical challenge to the development of improved pharmaceutical compositions and methods of treatment. Such challenges include, for example, difficulties in achieving formulation stability within the required pH limitations. These challenges are further complicated by the requirement that the pharmaceutical compositions and methods of treatment provide pharmacokinetically-appropriate and pharmacokinetically-consistent control of dopamine levels in the patient's brain.

In one embodiment, the pharmaceutical composition comprises a levodopa active agent in an amount of about 4.0 weight/weight percent of the total composition; a carbidopa active agent (e.g., carbidopa monohydrate) in an amount of about 1.0 weight/weight percent of the total composition; at least one suspending agent; and a liquid vehicle (for example, water). In various embodiments, the liquid vehicle can make up from about zero weight/weight percent to about 95 weight/weight percent of the total composition, for example from about 10 weight/weight percent to about 70 weight/weight percent, or from about 40 weight/weight percent to about 60 weight/weight percent of the total composition.

In one embodiment, the levodopa active agent is levodopa and pharmaceutically acceptable salts or hydrates thereof, such as levodopa monohydrate. Levodopa is preferably present in the composition in an amount of from about 1.0 to 5.0 weight/weight percent in the total composition. In a preferred embodiment the pharmaceutical composition comprises about 4.0 weight/weight percent of a levodopa active agent. In one embodiment, the levodopa active agent can be processed into microparticles or microspheres or the like, for example as described in Example 1 below, for inclusion in the present pharmaceutical compositions.

In one embodiment, the carbidopa active agent is carbidopa and pharmaceutically acceptable salts or hydrates thereof, such as carbidopa monohydrate. The carbidopa active agent is preferably present in the composition in an amount of from about 0.25 to 1.25 weight/weight percent in the total composition. In a preferred embodiment the pharmaceutical composition comprises about 1.0 weight/weight percent of a carbidopa active agent. The preferred form of carbidopa active agent to be administered is carbidopa monohydrate. In one embodiment, the carbidopa active agent can be processed into microparticles or microspheres or the like, for example as described in Example 1 below, for inclusion in the present pharmaceutical compositions.

The levodopa active agent and carbidopa active agent may be present in the pharmaceutical composition in any suitable ratio, for example, the ratio of levodopa active agent to carbidopa active agent (e.g., carbidopa monohydrate) in the present pharmaceutical compositions may be about 4:1. For example, the pharmaceutical composition can comprise about 4 weight/weight percent of levodopa active agent and 1 weight/weight percent carbidopa active agent (e.g., carbidopa monohydrate). In one embodiment, the pharmaceutical composition comprises a liquid or viscous liquid comprising about 200 mg levodopa and about 50 mg carbidopa (e.g., carbidopa monohydrate) per each 5.0 mL volume. In one embodiment, the levodopa active agent and the carbidopa active agent are processed into microparticles or microspheres or the like, for example as described in Example 1 below, for inclusion in the present pharmaceutical compositions.

The ratio of levodopa active agent, or of the combination of levodopa active agent to carbidopa active agent, to a suspending agent is from about 3 to about 1 w/w % to about 1 to about 30 w/w %, with a generally preferred range from about 2 to about 1 w/w % to about 1 to about 10 w/w %. Such readily available suspending agents are well known in the art and can include polymer-based suspending agents, such as, but not limited to, carbohydrate-based suspending agents and acrylic acid-based polymers (e.g., Carbomer, Carbopol®). Exemplary carbohydrate-based suspending agents include, but are not limited to hydroxypropylcellulose, hydroxymethylcellulose, and sodium carboxymethyl cellulose (NaCMC). Acrylic acid-based polymers may be cross-linked, for example, cross-linked with polyalkenyl ethers or divinyl glycol. In particular, the suspending agent may be sodium carboxymethyl cellulose (NaCMC) or Carbopol.

For the present compositions, one or more suspending agents can be used to obtain the ratios of levodopa active agent, or of the combination of levodopa active agent to carbidopa active agent, to suspending agent as set forth above.

However, when a surfactant is used, it may be best to add the surfactant or surfactants following addition of levodopa active agent and carbidopa active agent and suspending agent as taught herein.

It should be understood that each component comprising the compositions of the present invention must be pharmaceutically acceptable and utilized in a non-toxic concentration.

In one embodiment, the pharmaceutical composition is a viscous liquid composition. In one aspect, the pharmaceutical composition comprises water and is suitable for infusion.

In another embodiment, the pharmaceutical composition is an aqueous pharmaceutical composition having a levodopa active agent concentration of at least about 5 mg/mL. In one aspect, the levodopa active agent concentration is at least about 10 mg/mL. In another aspect, the levodopa active agent concentration is at least about 20 mg/mL. In another aspect, the levodopa active agent concentration is at least about 30 mg/mL. In another aspect, the levodopa active agent concentration is at least about 35 mg/mL. In another aspect, the levodopa active agent concentration is at least about 40 mg/mL. In another aspect, the levodopa active agent concentration is at least about 45 mg/mL. In another aspect, the levodopa active agent concentration is at least about 50 mg/mL. In another aspect, the levodopa active agent concentration is at least about 100 mg/mL. In another aspect, the levodopa active agent concentration is at least about 150 mg/mL. In another aspect, the levodopa active agent concentration is at least about 200 mg/mL.

In another embodiment, the pharmaceutical composition is an aqueous pharmaceutical composition having a carbidopa active agent (e.g., carbidopa monohydrate) concentration of at least about 5 mg/mL. In one aspect, the carbidopa active agent concentration is at least about 10 mg/mL. In another aspect, the carbidopa active agent concentration is at least about 20 mg/mL. In another aspect, the carbidopa active agent concentration is at least about 30 mg/mL. In another aspect, the carbidopa active agent concentration is at least about 50 mg/mL. In another aspect, the carbidopa active agent concentration is at least about 100 mg/mL. In another aspect, the carbidopa active agent concentration is at least about 150 mg/mL. In another aspect, the active agent carbidopa concentration is at least about 200 mg/mL.

The pharmaceutical compositions of the present disclosure optionally comprise one or more additional pharmaceutically acceptable excipients. The term "excipient" refers to any substance, not itself a therapeutic agent, used as a carrier or vehicle for delivery of a therapeutic agent to a subject or added to a pharmaceutical composition to improve its handling or storage properties or to permit or facilitate formation of a unit dose of the composition. Excipients include, for example, antioxidants, agents to adjust the pH and osmolarity, preservatives, thickening agents, colorants, buffering agents, bacteriostats, and stabilizers. A given excipient, if present, generally will be present in an amount of about 0.001% to about 95%, about 0.01% to about 80%, about 0.02% to about 25%, or about 0.3% to about 10%, by weight.

In one embodiment, the pharmaceutical compositions optionally comprise an antioxidant. Suitable antioxidants for use in the pharmaceutical compositions include, for example, butylated hydroxytoluene, butylated hydroxyanisole, potassium metabisulfite, cysteine, and the like.

In one embodiment, the pharmaceutical compositions optionally comprise a buffering agent. Buffering agents include agents that reduce pH changes. Suitable classes of buffering agents for use in various embodiments of the present invention comprise a salt of a Group IA metal including, for example, a bicarbonate salt of a Group IA metal, a carbonate salt of a Group IA metal, an alkaline or alkali earth metal buffering agent, an aluminum buffering agent, a calcium buffering agent, a sodium buffering agent, or a magnesium buffering agent. Suitable buffering agents further include carbonates, phosphates, bicarbonates, citrates, borates, acetates, phthalates, tartrates, succinates of any of the foregoing, for example, sodium or potassium phosphate, citrate, borate, acetate, bicarbonate and carbonate.

In one embodiment, the composition has a pH from about 3.5 to about 8. In one aspect, the pH is from about 3.5 to about 7.5. In another aspect, the pH is from about 4.0 to about 7.5. In another aspect, the pH is from about 5.0 to about 7.5. In another aspect, the pH is from about 5.5 to about 7.5. In another aspect, the pH is from about 6.0 to about 7.5.

In various embodiments, the pharmaceutical composition may be present in a container. Suitable containers include containers (e.g., a bag) with lower oxygen permeability (e.g., oxygen transmission rate of ~0.95 cc/(100 in$^2$*day)) or which are oxygen impermeable. These low oxygen permeability barriers may be incorporated into the primary container of a secondary outer container. Non-limiting examples of suitable containers include DDR (Disposable Drug Reservoirs) bags, such as an EVA/EVOH/EVA bag.

In still other embodiments, the present disclosure relates to a ready-to-use vial or cartridge or container or enclosure suitable for liquid pharmaceutical dosage formulation containment. Such container may serve the function of holding a liquid formulation containing one or more active ingredients. The vials can also serve as storage for powder forms of the active ingredients such that the vial can be in a ready to use format wherein reconstitution with an aqueous vehicle results in a ready-to-withdraw or ready-to-load injection to the patient.

In another embodiment, a pharmaceutical dosage form is provided. The pharmaceutical dosage form may comprise the pharmaceutical composition described herein in a DDR having an oxygen impermeable enclosure disposed therein, wherein the oxygen impermeable enclosure is purged with an inert gas (e.g., $N_2$). An oxygen scavenger (e.g., ferrous or non-ferrous based, canister or sachet) may also be added. The pharmaceutical dosage form may suitable for use in a continuous infusion pump capable of delivering the composition in a therapeutically effective manner. A suitable oxygen impermeable enclosure can include, for example, a foil bag or a bag having an EVA-EVOH film layer.

III. Methods of Preparing a Pharmaceutical Composition

The present disclosure further relates to methods of preparing the pharmaceutical compositions described herein. In various aspects, the methods of preparing the pharmaceutical composition describe herein can comprise providing a levodopa active agent and a carbidopa active agent in suitable amounts so that the levodopa active agent and carbidopa active agent are present in therapeutically effective amounts in the pharmaceutical composition. The levodopa active agent and carbidopa active agent may be added to water to produce a slurry. The slurry may be added to one or more suspending agents (e.g., NaCMC) as described herein to form a suspension. The suspension may or may not undergo $N_2$ sparging to reduce the oxygen level. Particularly, the suspension may be subjected to $N_2$ sparging. Optionally, the suspension may be degassed to remove any entrapped nitrogen or air from the suspension. The suspension may then be loaded into lower oxygen permeability or oxygen impermeable containers as described herein. Optionally, an oxygen scavenger may be added to the suspension as well. The combination of $N_2$ sparging of the suspension and use of lower oxygen permeability containers advantageously can result in a pharmaceutical composition with increased chemical stability by reducing both the initial solubilized $O_2$ present in the composition and the amount of $O_2$ ingress into the composition during storage.

Additionally, when the suspension is subjected to $N_2$ sparging and/or the container has low oxygen permeability, the pharmaceutical composition may not experience degradation into DHPA at a rate faster than 0.04 w/w % per week of refrigerated storage conditions. (The percent is relative to the label amount of carbidopa.) Additionally or alternatively, when the suspension is subjected to $N_2$ sparging and/or the container has low oxygen permeability, the pharmaceutical composition may not experience degradation into DHPPA at a rate faster than 0.04 w/w % per week of refrigerated storage conditions. (The percent is relative to the label amount of carbidopa.) Additionally or alternatively, when the suspension is subjected to $N_2$ sparging and/or the container has low oxygen permeability, the pharmaceutical composition may not degrade producing hydrazine at a rate faster than 0.6 µg/g per week per week of refrigerated storage, where µg/g denotes µg of hydrazine per gram of gel-suspension.

In various aspects, the levodopa active agent (e.g., prior to forming the suspension) may have a particle size distribution where:
(i) D50 may be less than or equal to about 5 µm, less than or equal to about 3 µm, or less than or equal to about 1 µm;
(ii) D90 may be less than or equal to about 11 µm, less than or equal to about 9 µm, less than or equal to about 7 µm, less than or equal to about 5 µm or less than or equal to about 3 µm; and
(iii) D100 may be less than or equal less than or equal to about 22 µm, less than or equal to about 21 µm, less than or equal to about 19 µm, less than or equal to about 17 µm, less than or equal to about 15 µm, less than or equal to about 13 µm or less than or equal to about 11 µm.

In particular, the levodopa active agent may have a particle size distribution of: (i) D50 less than or equal to about 5 µm; (ii) D90 less than or equal to 11 µm; and (iii) D100 less than or equal to 22 µm.

Additionally, the carbidopa active agent (e.g., prior to forming the suspension) may have a particle size distribution where:
(i) D50 may be less than or equal to 3 µm;
(ii) D90 may be less than or equal to 7 µm, or less than or equal to 5 µm; and
(iii) D100 may be less than or equal to 21 µm, less than or equal to 19 µm, less than or equal to 17 µm, less than or equal to 15 µm, less than or equal to 13 µm, less than or equal to 11 µm, less than or equal to 9 µm.

In particular, the carbidopa active agent may have a particle size distribution of: (i) D50 less than or equal to about 3 µm; (ii) D90 less than or equal to 7 µm; and (iii) D100 less than or equal to 21 µm. The levodopa active agent and/or the carbidopa active may be milled or micronized to achieve such a particle size distribution.

Advantageously, the levodopa active agent and the carbidopa active agent with the above described particle size distributions may successfully form a suspension and maintain physical stability of the suspension throughout the pharmaceutical composition's shelf life even when the levodopa active agent and the carbidopa active agent are present at higher concentrations in the composition. For example, physical stability may be maintained even when the pharmaceutical composition comprises about 4 weight/weight percent of levodopa active agent and 1 weight/weight percent carbidopa active agent (e.g., carbidopa monohydrate).

In another embodiment, pharmaceutical compositions as described herein prepared by the methods described herein are provided. In particular, a levodopa active agent and a carbidopa active agent may be provided in suitable amounts so that the levodopa active agent and carbidopa active agent are present in therapeutically effective amounts in the pharmaceutical composition. The levodopa active agent and the carbidopa active agent provided have a particle size distribution as described above. The levodopa active agent and carbidopa active agent are added to water to produce a slurry. The slurry is added to a suspending agent (e.g., NaCMC) as described herein or a mixture of suspending agents to form a suspension, and the suspension can undergo $N_2$ sparging to reduce the oxygen level. The suspension can be loaded into lower oxygen permeability or oxygen impermeable containers as described herein. Optionally, an oxygen scavenger may be added to the suspension as well.

IV. Methods of Treatment

The present disclosure further relates to methods of treating Parkinson's disease and associated conditions comprising administering a therapeutically effective amount of a pharmaceutical composition comprising a high concentration levodopa active agent and carbidopa active agent to a patient. A pharmaceutical composition comprising a high concentration levodopa active agent and carbidopa active agent can comprise, for example, a liquid or viscous liquid comprising about 200 mg levodopa and about 50 mg carbidopa monohydrate per each 5.0 mL volume.

In one embodiment, the present disclosure relates to a method of treating a condition in need of treatment, wherein the method comprises administering to the patient a therapeutically effective amount of a pharmaceutical composition of the present disclosure.

In one embodiment, the condition treated by administering the pharmaceutical composition is Parkinson's disease.

In another embodiment, the condition treated by administering the pharmaceutical composition is impaired motor performance in a patient with Parkinson's disease (i.e., a method of improving motor performance in a patient with Parkinson's disease).

In another embodiment, the pharmaceutical composition is administered to treat motor fluctuations in a patient with Parkinson's disease.

In another embodiment, the pharmaceutical composition is administered to treat dyskinesia in a patient with Parkinson's disease.

In another embodiment, the present pharmaceutical compositions are administered via intestinal administration. They can be administered (or "infused") directly into the intestine, such as the small intestine (e.g., duodenum or the jejunum) by a permanent tube inserted via percutaneous endoscopic gastrostomy, for example, with an outer transabdominal tube and an inner intestinal tube. In one aspect, the first compound and the second compound are administered via a tube inserted by radiological gastrojejunostomy. In another aspect, the present pharmaceutical compositions are administered via a temporary nasoduodenal tube that is inserted into the patient, for example to initially to determine if the patient responds favorably to the treatment method before the permanent tube is inserted.

In embodiments where one or more of the present pharmaceutical compositions are administered via intestinal administration, administration can be carried out using a portable pump, such as the pump sold under the trade name, CADD-Legacy Duodopa® pump. Specifically, a cassette, pouch, vial or cartridge comprising the first compound and the second compound can be attached to the pump to create the delivery system. The delivery system is then connected to the nasoduodenal tube, the transabdominal port, the duodenal tube, or the jejunum tube for intestinal administration.

In one embodiment, the method comprises administering one or more of the present pharmaceutical compositions to the patient substantially continuously over a period of at least about 12 hours. In additional aspects, the present pharmaceutical compositions can be administered substantially continuously over a period of about 16 hours, about 24 hours, about 36 hours, about 48 hours, about 3 days, about 4 days, about 5 days, about 6 days, about one week, or longer.

In one embodiment, the dosing of the present pharmaceutical composition administered to the patient is adjusted to optimize the clinical response achieved by a patient, which means, for example, maximizing the functional ON-time during the day by minimizing the number and duration of OFF-time episodes (i.e., bradykinesia) and minimizing ON-time with disabling dyskinesia.

In one embodiment, the daily dose of levodopa active agent administered to the patient according to methods of the present disclosure may be, for example, about 20 to about 5000 mg, about 20 mg to about 4000 mg, about 20 mg to about 3000 mg, about 20 mg to about 2000 mg, or about 20 mg to about 1000 mg per day. In various aspects, the patient may receive, for example, about: 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 mg of levodopa active agent per day.

In one embodiment, the daily dose of the carbidopa active agent administered to the patient according to methods of the present disclosure may be, for example, 0 to about 625 mg, 0 mg to about 500 mg, 0 mg to about 375 mg, 0 mg to about 250 mg, or 0 mg to about 125 mg per day. In various aspects, the patient may receive, for example, about: 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, or 1250 mg of carbidopa active agent per day.

In some embodiments, an amount of levodopa active agent and carbidopa active agent are administered such that in combination they are sufficient to achieve an L-dopa plasma level in the patient of at least about 100 ng/mL. In one aspect, the L-dopa plasma level is at least about 200 ng/mL. In another aspect, the L-dopa plasma level is at least about 200 ng/mL. In another aspect, the L-dopa plasma level is at least about 300 ng/mL. In another aspect, the L-dopa plasma level is at least about 400 ng/mL. In another aspect, the L-dopa plasma level is at least about 500 ng/mL. In another aspect, the L-dopa plasma level is at least about 600 ng/mL. In another aspect, the L-dopa plasma level is at least about 700 ng/mL. In another aspect, the L-dopa plasma level is at least about 800 ng/mL. In another aspect, the L-dopa plasma level is at least about 900 ng/mL. In another aspect, the L-dopa plasma level is at least about 1,000 ng/mL. In another aspect, the L-dopa plasma level is at least about 1,500 ng/mL. In another aspect, the L-dopa plasma level is at least about 2,000 ng/mL. In another aspect, the L-dopa plasma level is at least about 3,000 ng/mL. In another aspect, the L-dopa plasma level is at least about 4,000 ng/mL. In another aspect, the L-dopa plasma level is at least about 5,000 ng/mL.

In some embodiments, an amount of the levodopa active agent and carbidopa active agent are administered such that in combination they are sufficient to achieve an L-dopa plasma level from about 10 ng/mL to about 8,000 ng/mL. In one aspect, the L-dopa plasma level is from about 25 ng/mL to about 6,000 ng/mL. In another aspect, the L-dopa plasma level is from about 50 ng/mL to about 4,000 ng/mL. In another aspect, the L-dopa plasma level is from about 100 ng/mL to about 2,000 ng/mL. In another aspect, the L-dopa plasma level is from about 25 ng/mL to about 1,200 ng/mL. In another aspect, the L-dopa plasma level is from about 10 ng/mL to about 500 ng/mL. In another aspect, the L-dopa plasma level is from about 25 ng/mL to about 500 ng/mL.

In some embodiments, the above-described L-dopa concentration ranges are maintained for at least about: a 1 hour interval, a 2 hour interval, a 3 hour interval, a 4 hour interval, a 5 hour interval, a 6 hour interval, a 7 hour interval, an 8 hour interval, a 9 hour interval, a 10 hour interval, an 11 hour interval, a 12 hour interval, an 18 hour interval, or a 24 hour interval.

In some embodiments, an amount of the levodopa active agent and carbidopa active agent are administered such that in combination they are sufficient to maintain a carbidopa plasma level less than about 500 ng/mL. In one aspect, the carbidopa plasma level is less than about 250 ng/mL. In another aspect, the carbidopa plasma level is less than about 100 ng/mL. In another aspect, the carbidopa plasma level is less than about 50 ng/mL. In another aspect, the carbidopa plasma level is less than about 25 ng/mL.

In some embodiments, an amount of the levodopa active agent and carbidopa active agent are administered such that in combination they are sufficient to maintain a carbidopa plasma level from about 1 to about 10 ng/mL. In one aspect, the carbidopa plasma level is from about 1 to about 25 ng/mL. In another aspect, the carbidopa plasma level is from about 1 to about 50 ng/mL. In another aspect, the carbidopa plasma level is from about 1 to about 100 ng/mL. In another aspect, the carbidopa plasma level is from about 1 to about 250 ng/mL. In another aspect, the carbidopa plasma level is from about 5 to about 250 ng/mL. In another aspect, the carbidopa plasma level is from about 5 to about 100 ng/mL. In another aspect, the carbidopa plasma level is from about 10 to about 250 ng/mL. In another aspect, the carbidopa plasma level is from about 10 to about 100 ng/mL. In another aspect, the carbidopa plasma level is from about 25 to about 250 ng/mL. In another aspect, the carbidopa plasma level is from about 25 to about 100 ng/mL.

In some embodiments, the above-described carbidopa concentration ranges are maintained for at least about: a 1 hour interval, a 2 hour interval, a 3 hour interval, a 4 hour interval, a 5 hour interval, a 6 hour interval, a 7 hour interval, an 8 hour interval, a 9 hour interval, a 10 hour interval, an 11 hour interval, a 12 hour interval, an 18 hour interval, or a 24 hour interval.

In additional embodiments, the levodopa active agent and the carbidopa active agent administered may have a particle size distribution of as described above.

In various embodiments, the pharmaceutical composition may be present in a container as described above and prior to administration to the patient, the gel-suspension may or may not be subjected to $N_2$ sparging. When the gel-suspension is subjected to $N_2$ sparging and the container has low oxygen permeability, the pharmaceutical composition may not experience degradation producing DHPA at a rate faster than 0.04 w/w % per week of refrigerated storage. (The percent is relative to the label amount of carbidopa.) Additionally or alternatively, when the container is subjected to $N_2$ sparging, the pharmaceutical composition may not experience degradation producing DHPPA at a rate faster than 0.04 w/w % per week of refrigerated storage. (The percent is relative to the label amount of carbidopa.) Additionally or alternatively, when the container is subjected to $N_2$ sparging, the pharmaceutical composition may not degrade producing hydrazine at a rate faster than 0.6 μg/g per week of refrigerated storage, where μg/g denotes μg of hydrazine per gram of gel-suspension.

V. Co-Administration of Additional Therapeutic Agents

The methods of treatment of the present disclosure optionally can further comprise administration of one or more therapeutic agents for the treatment of Parkinson's disease in addition to administration of the levodopa active agent and carbidopa active agent. In one embodiment, the additional therapeutic agent(s) is selected from the group consisting of decarboxylase inhibitors other than a carbidopa active agent (e.g., benserazide), catechol-0-methyl transferase ("COMT") inhibitors (e.g., entacapone and tolcapone), and monoamine oxidase A ("MAO-A") or monoamine oxidase B ("MAO-B") inhibitors (e.g., moclobemide, rasagiline, selegiline, and safinamide). In one aspect, the additional therapeutic agent(s) is selected from the group consisting of decarboxylase inhibitors other than a carbidopa active agent. In another aspect, the additional therapeutic agent(s) is selected from the group consisting of COMT inhibitors. In another aspect, the additional therapeutic agent(s) is selected from the group consisting of MAO-A inhibitors. In another aspect, the additional therapeutic agent(s) is selected from the group consisting of MAO-B inhibitors.

In a similar manner, the pharmaceutical compositions of the present disclosure optionally can further comprise one or more additional therapeutic agents for the treatment of Parkinson's disease as described above.

VI. Kits

The present disclosure also relates to kits comprising one or more pharmaceutical dosage forms comprising a carbidopa active agent; kits comprising one or more pharmaceutical dosage forms comprising a levodopa active agent; and kits comprising one or more pharmaceutical dosage forms comprising both a levodopa active agent and carbidopa active agent. In the kit, the pharmaceutical dosage forms may be present, separately or together, in a lower $O_2$ permeability bag. The pharmaceutical dosage forms may comprise a high concentration of a levodopa active agent and a carbidopa active agent, for example, a levodopa active agent in an amount of about 4.0 weight/weight percent of the total composition; and a carbidopa monohydrate active agent in an amount of about 1.0 weight/weight percent of the total composition. The kit optionally can comprise one or more additional therapeutic agents and/or instructions, for example, instructions for using the kit to treat a patient having Parkinson's disease or an associated condition.

VII. Examples

The following non-limiting examples are provided to further illustrate the present disclosure. Abbreviations used in the examples below include the following:

"Cmax" means maximum observed plasma concentration.

"Tmax" means time to maximum observed plasma concentration.

"AUC" means area under the plasma concentration-time curve.

"$t_{1/2}$" means biological half-life, i.e., the time required for half the quantity of a drug or other substance administered to a living organism to be metabolized or eliminated by normal biological processes.

Example 1

Preparation of Pharmaceutical Composition

A high concentration ("HC") levodopa active agent/carbidopa active agent pharmaceutical composition was prepared as shown in FIG. 1 and as described below:

1.1 Gel Preparation

Pre-work was performed in the lab to establish the ratio of NaCMC 700 to NaCMC 2000 needed to achieve a certain viscosity. The viscosity was measured with a rotational viscometer at two points: 22° C. at 24.1 1/s (also called the "high shear viscosity"); and at 5° C. at 0.1 1/s (also called the "low shear viscosity"). The proper amounts of NaCMC 2000 and NaCMC 700 were then dispensed and added to a hopper, after which the NaCMC was fed into the homogenizer tank and mixed at a high shear. The gel was then degassed and visually inspected to ensure that the NaCMC dissolved. This was also the time that the gel is sampled for viscosity measurements.

1.2 Gel Sparging

Gel was sparged with nitrogen to remove the majority of oxygen prior to adding the API (Levodopa and Carbidopa). Oxygen concentration was monitored throughout the process via an inline oxygen probe.

1.3 First Slurry Preparation

Half of Levodopa and Carbidopa was added to water in a separate vessel and was mixed using one overhead impeller and one bottom driven impeller. This method is considered low shear. Alternatively the overhead impeller can be replaced with a homogenizer for achieving high shear mixing. The slurry was used to wet and delump the API. After the process was finished, the slurry was transferred to the homogenizer tank.

1.4 Gel Suspension Preparation

This is where the API from the slurry and the NaCMC gel was mixed, under high shear, to achieve a homogeneous suspension. Nitrogen was sparged into the tank to reduce the oxygen level that was initially introduced with the slurry transfer.

1.5 Second Slurry Preparation

The other half of Levodopa and Carbidopa was added to water and mixed similar to the process in step 1.3.

1.6 Gel Suspension Preparation

The API from the second slurry was mixed with the rest of the gel suspension at the same conditions as in step 1.4. Nitrogen was sparged into the tank to reduce the oxygen level that was initially introduced with the slurry transfer.

1.7 Degassing

The gel suspension was degassed to remove any entrapped nitrogen or air from the gel.

1.8 Filling

The filling lines were first flushed with nitrogen before gel suspension was pushed through. 55-61 g of gel suspension was filled into disposable drug reservoirs (DDRs). Fill weight was checked at routine intervals via a balance. Oxygen reading was taken at the filling nozzle (for the two case studies, the reading was taken at the discharge end).

1.9 Packaging

DDRs were labeled and packaged into a kit that holds 7 DDRs. The kit protects the formulation from light. The kits were then sent to the freezer.

TABLE 1

Formulation of High Concentration (HC) and Low Concentration (LC) Pharmaceutical Composition

| Component | HC w/w % | LC w/w % |
|---|---|---|
| Levodopa Micronized | 4 | 2 |
| Carbidopa Monohydrate Micronized | 1 | 0.5 |
| NaCMC 2000 | 2.92* | 2.92* |
| NaCMC 700 | | |
| Purified Water | 92.08 | 94.58 |

*Represents total NaCMC. The ratio of one NaCMC grade to the other can be varied to achieve the desired viscosity.
**Density of HC formulation was approximately 1.03 g/ml and LC formulation is approximately 1.02 g/ml

TABLE 2

LC Specifications and HC Tentative Ranges for Drug Product and API Attributes

| Drug Product Attributes | LC Specs | HC Tentative Range |
|---|---|---|
| High Shear Viscosity (22° C. and 24.1 1/s) | 2000-3500 cps | ≤4500 cps |
| Low Shear Viscosity (5° C. and 0.1 1/s) | >21000 cps | ≥45000 cps |
| pH | 5.5-7.5 | |
| Oxygen Concentration | Ambient | Low |
| Batch Size | 500 Kg | |

Example 2

High Concentration Pharmaceutical Composition Stability 2.1—A high concentration (HC) formulation was made on the commercial scale equipment to improve the nitrogen sparging process time and mixing efficiency. The overall manufacturing process was the same as in Example 1. A high viscosity was chosen, relative to the HC formulation viscosity range, to ensure good physical stability. The batch was filled into prototype DDR (Disposable Drug Reservoirs) bags (without the housing) and placed on stability. The bags are made with a 0.3 mm thick EVA/EVOH/EVA multilayer film. This batch maintained its chemical and physical stability throughout the 15 week stability study.

TABLE 3

Raw Material and Finished Material Attributes

| Suspension Attributes | Value |
|---|---|
| High Shear Viscosity (24.1 1/s, 22° C.) | 43000 cps |
| Low Shear Viscosity (0.1 1/s, 5° C.) | 49600 cps |
| pH | 6.4* |
| Oxygen Concentration | 0.45* mg/L |
| Batch Size | 500 Kg |

*Values were measured in process 2.2—Analytical Results

Batch Content Uniformity—100 mL of the pharmaceutical composition was filled into cassettes at the beginning, middle, and end of the filling run which represents bottom, middle, and top of the tank, respectively. These cassettes were then assayed and the results represent the content uniformity of the batch.

TABLE 4

Batch Content Uniformity Results (API concentration)

| Cassettes | Levodopa % | Carbidopa % |
|---|---|---|
| Beginning 1 | 94.9 | 94.6 |
| Beginning 2 | 101.9 | 101.6 |
| Beginning 3 | 99.5 | 99.0 |
| Beginning 4 | 98.7 | 98.4 |
| Beginning 5 | 99.7 | 99.4 |
| Middle 1 | 101.8 | 101.6 |
| Middle 2 | 99.7 | 99.3 |

TABLE 4-continued

Batch Content Uniformity Results (API concentration)

| Cassettes | Levodopa % | Carbidopa % |
|---|---|---|
| Middle 3 | 99.1 | 99.0 |
| Middle 4 | 96.0 | 95.8 |
| Middle 5 | 101.2 | 100.9 |
| End 1 | 101.3 | 101.0 |
| End 2 | 101.6 | 101.4 |
| End 3 | 101.6 | 101.3 |
| End 4 | 101.7 | 101.5 |
| End 5 | 101.8 | 101.6 |

2.3—Formulation Attributes on Stability

Filled DDR bags were frozen and stored at −20° C. after manufacture. Bags for testing were then placed at 5° C. for a 15 week stability study. Samples were evaluated at 0, 8, and 15 weeks. In addition, a portion of the samples were subsequently placed at 30° C. in 75% relative humidity (% RH), after they spent either 8 or 15 weeks at 5° C., with testing at 24 and 48 hours. Assay, impurities, pH, and viscosity were all tested. Results are summarized in Table 5 below.

TABLE 5

Assay, Impurities, pH, and Viscosity Throughout a 15 Weeks Stability Study

| Condition | Levodopa Assay (%) | Carbidopa Assay (%) | % DHPA per Carbidopa | % DHPPA per Carbidopa |
|---|---|---|---|---|
| 5° C.: 0 weeks | 102.3 | 100.5 | 0.14 | 0.06 |
| 5° C.: 8 weeks | 104.3 | 102.7 | 0.44 | 0.42 |
| 5° C.: 8 weeks 30° C.: 24 hrs | 102.4 | 100.9 | 0.46 | 0.41 |
| 5° C.: 8 weeks 30° C.: 48 hrs | 103 | 101.4 | 0.50 | 0.47 |
| 5° C.: 15 weeks | 102.1 | 99.8 | 0.60 | 0.60 |
| 5° C.: 15 weeks 30° C.: 24 hrs | 102.5 | 100 | 0.74 | 0.80 |
| 5° C.: 15 weeks 30° C.: 48 hrs | 102.2 | 99.7 | 0.74 | 0.79 |

| Condition | Hydrazine (μg) per gel (g) | pH | Viscosity (cps) at 22° C. and 24.1 sec$^{-1}$ | Viscosity (cps) at 5° C. and 0.1 sec$^{-1}$ |
|---|---|---|---|---|
| 5° C.: 0 weeks | 2.10 | 6.4 | 4400 | 49600 |
| 5° C.: 8 weeks | 6.63 | 6.4 | 4500 | 57400 |
| 5° C.: 8 weeks 30° C.: 24 hrs | 7.43 | 6.3 | 4500 | 59900 |
| 5° C.: 8 weeks 30° C.: 48 hrs | 9.90 | 6.4 | 4500 | 54200 |
| 5° C.: 15 weeks | 9.20 | 6.3 | 4400 | 58300 |
| 5° C.: 15 weeks 30° C.: 24 hrs | 10.90 | 6.3 | 4400 | 59000 |
| 5° C.: 15 weeks 30° C.: 48 hrs | 11.10 | 6.3 | 4500 | 55200 |

2.4—Uniformity of Dispensed Content of Samples on Stability

The uniformity of dispensed content (UDC) method was used to obtain API concentration in the gel as it is dosed. This simulates what a patient would be receiving per every 5 g of gel delivered by the pump, and ensures that a patient will be receiving consistent amounts of drug throughout the consumption of one DDR. The test was performed at each time point throughout the 15 week stability. Particle size distributions of the APIs used for the study were within the particle size limits mentioned herein. Results are summarized in Tables 6 (levodopa) and 7 (carbidopa) below.

TABLE 6

Uniformity of Dispensed Content of Levodopa Samples on Stability

| Dispensed Fraction | 5° C.: 0 weeks | 5° C.: 8 weeks | 5° C.: 8 weeks 30° C.: 24 hrs | 5° C.: 8 weeks 30° C.: 48 hrs | 5° C.: 15 weeks | 5° C.: 15 weeks 30° C.: 24 hrs | 5° C.: 15 weeks 30° C.: 48 hrs |
|---|---|---|---|---|---|---|---|
| 1 | 102.1 | 103.0 | 103.5 | 103.3 | 101.6 | 100.7 | 102.6 |
| 2 | 102.1 | 102.0 | 102.8 | 102.6 | 99.8 | 100.6 | 101.4 |
| 3 | 100.0 | 103.4 | 103.3 | 103.1 | 98.7 | 100.6 | 102.2 |
| 4 | 101.9 | 103.4 | 103.3 | 103.7 | 99.0 | 101.6 | 101.9 |
| 5 | 101.6 | 103.1 | 102.0 | 102.8 | 98.9 | 101.9 | 102.0 |
| 6 | 101.6 | 103.6 | 104.0 | 99.7 | 103.1 | 100.9 | 102.0 |
| 7 | 101.9 | 103.6 | 104.1 | 103.7 | 101.7 | 97.3 | 102.4 |
| 8 | 101.2 | 104.0 | 104.5 | 103.7 | 101.9 | 102.7 | 102.6 |
| 9 | 100.1 | 104.1 | 104.0 | 104.3 | 102.2 | 102.4 | 102.5 |
| 10 | 99.6 | 103.7 | 104.4 | 103.7 | 102.1 | 104.1 | 102.0 |

TABLE 7

Uniformity of Dispensed Content of Carbidopa Samples on Stability

| Dispensed Fraction | 5° C.: 0 weeks | 5° C.: 8 weeks | 5° C.: 8 weeks 30° C.: 24 hrs | 5° C.: 8 weeks 30° C.: 48 hrs | 5° C.: 15 weeks | 5° C.: 15 weeks 30° C.: 24 hrs | 5° C.: 15 weeks 30° C.: 48 hrs |
|---|---|---|---|---|---|---|---|
| 1 | 102.0 | 102.5 | 102.4 | 101.4 | 100.4 | 98.5 | 99.7 |
| 2 | 102.0 | 100.9 | 101.3 | 101.3 | 98.6 | 98.8 | 99.1 |
| 3 | 99.5 | 102.0 | 101.5 | 101.2 | 96.9 | 98.1 | 99.5 |
| 4 | 101.0 | 101.7 | 101.5 | 101.7 | 97.0 | 99.4 | 99.2 |
| 5 | 100.5 | 101.6 | 100.1 | 100.5 | 96.8 | 99.4 | 99.4 |
| 6 | 100.8 | 102.0 | 101.6 | 97.7 | 99.5 | 98.3 | 99.3 |
| 7 | 100.9 | 102.0 | 101.8 | 101.8 | 98.1 | 94.7 | 99.3 |
| 8 | 100.3 | 101.9 | 101.7 | 101.3 | 99.2 | 99.8 | 99.3 |
| 9 | 99.3 | 101.9 | 101.8 | 101.7 | 98.7 | 99.3 | 99.4 |
| 10 | 98.4 | 101.7 | 101.7 | 101.5 | 99.3 | 100.8 | 99.1 |

Example 3

Therapeutic Effect of Pharmaceutical Composition in Mini-Pigs

Figure 2:
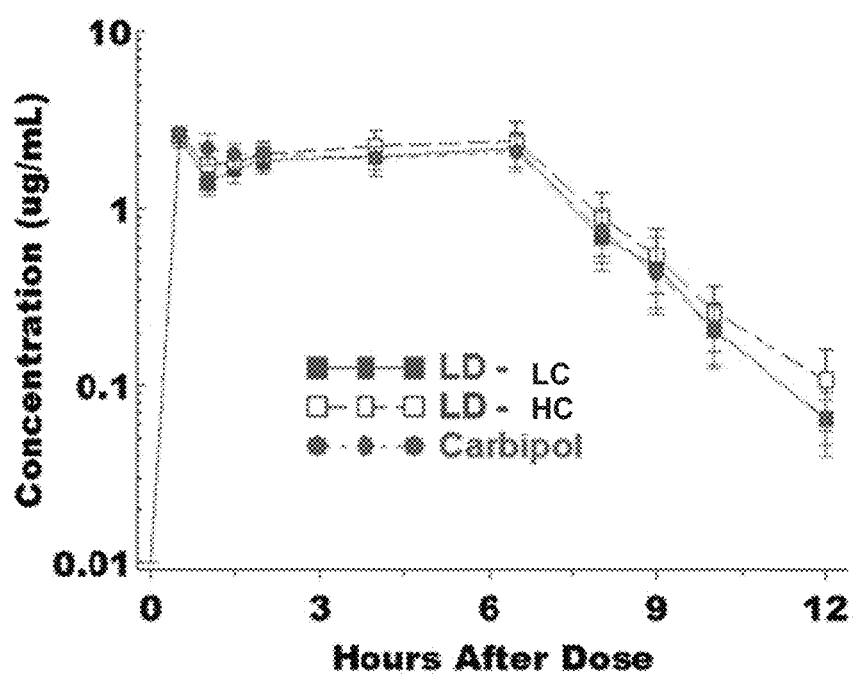
FIG. 2 shows the L-Dopa blood level time-concentration profile in mini-pigs of an exemplary pharmaceutical composition of the invention as against two comparators, all given in a six-hour continuous infusion.
Figure 3:
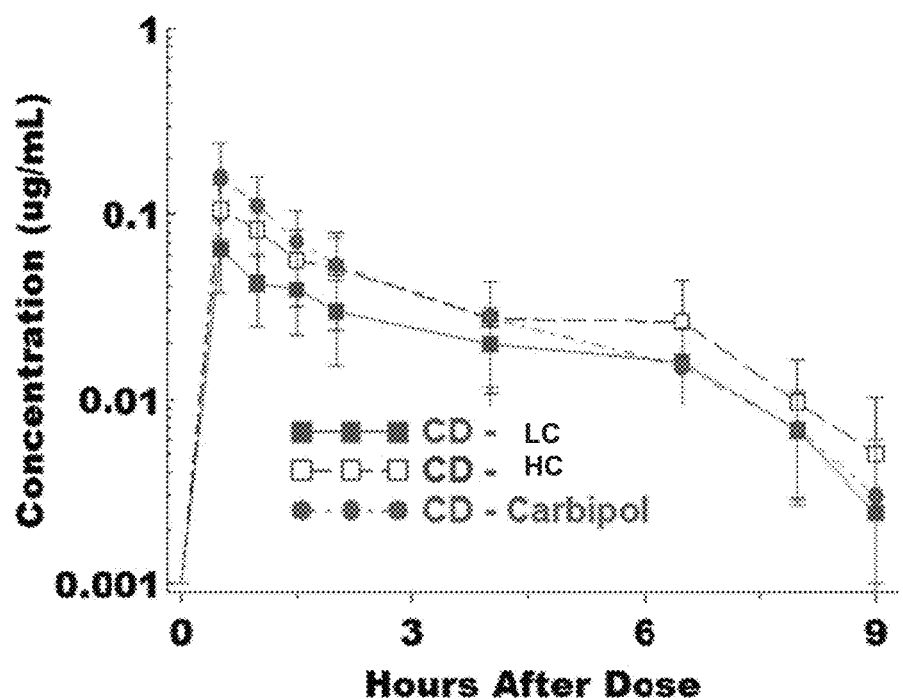
FIG. 3 shows the carbidopa blood level time-concentration profile in mini-pigs of an exemplary pharmaceutical composition of the invention as against two comparators, all given in a six-hour continuous infusion.

High concentration L-dopa/carbidopa intestinal gel was compared with a low concentration L-dopa/carbidopa intestinal gel and tested in the following manner. A group of four minipigs each was administered LC L-dopa/carbidopa intestinal gel, HC L-Dopa/carbidopa intestinal gel, or L-dopa/carbidopa in a Carbopol carrier in a cross-over study design. Each of four mini-pigs was administrated with one formulation at the first day of a week, followed by 1-week washout period before the second formulation was administered. The third formulation was administered to the same mini-pigs after another week of washout period.
Total Dose: 11.07 mg/kg levodopa dose over 6.5 hrs.; 20 mg/mL
Groups: LC; HC; Carbopol
Bolus dose: 2.53 mg/kg over 30 min Bolus dose
Infusion dose: 8.54 mg/kg over 6 hrs.
  Bolus Infusion Rate:
    LC=0.253 mL/kg/hr (For example: 10 kg pig=2.53 mL/hr pump rate)
    HC=0.127 mL/kg/hr (For example: 10 kg pig=1.27 mL/hr pump rate)
    Carbopol=0.127 mL/kg/hr (For example: 10 kg pig=1.27 mL/hr pump rate)
  6 hr Infusion Rate:
    LC=0.071 mL/kg/hr (For example: 10 kg pig=0.71 mL/hr pump rate)
    HC=0.0355 mL/kg/hr (For example: 10 kg pig=0.355 mL/hr pump rate)
    Carbopol=0.0355 mL/kg/hr (For example: 10 kg pig=0.355 mL/hr pump rate).
Plasma sampling Time points: 0.5, 1, 1.5, 2, 4, 6, 8, 9, 10, 12 h The results of the study confirm that the high concentration levodopa/carbidopa intestinal gel demonstrates comparable $C_{max}$, $T_{max}$ and AUC values to the LC formulation when administered under half hour bolus and 6 hour infusion conditions, as shown in FIGS. 2 and 3. Cassettes of levodopa at 11.07 mg/kg and of carbidopa monohydrate at 2.77 mg/kg were dosed at 80 µL/kg (LC gel) or 40 µL/kg (HC gel and Carbopol control). Bioavailability of levodopa is summarized in Table 8 below. The half lives in Table 8 are calculated as harmonic means.

TABLE 8

Levodopa plasma concentration

| Parameter | Pig 1 | Pig 2 | Pig 3 | Pig 4 | Mean (SEM) | |
|---|---|---|---|---|---|---|
| $C_{max}$ (µg/mL) | 3.36 | 2.84 | 2.30 | 2.25 | 2.69 (0.26) | LC gel |
| $T_{max}$ (h) | 6.5 | 0.5 | 0.5 | 0.5 | 2.0 (1.5) | |
| AUC (µg · h/mL) | 23.7 | 19.1 | 10.4 | 10.2 | 15.9 (3.35) | |
| $t_{1/2}$ (h) | 1.0 | 0.9 | 0.9 | 2.2 | 1.1 | |
| $C_{max}$ (µg/mL) | 4.23 | 3.09 | 1.70 | 2.45 | 2.87 (0.53) | HC gel |
| $T_{max}$ (h) | 6.5 | 4.0 | 0.5 | 0.5 | 2.9 (1.5) | |
| AUC (µg · h/mL) | 27.6 | 21.8 | 9.88 | 12.3 | 17.9 (4.13) | |
| $t_{1/2}$ (h) | 1.3 | 1.1 | 1.0 | 1.3 | 1.2 | |
| $C_{max}$ (µg/mL) | 3.03 | 3.39 | 1.95 | 2.62 | 2.75 (0.31) | Carbopol |
| $T_{max}$ (h) | 6.5 | 1.0 | 0.5 | 0.5 | 2.1 (1.5) | |

TABLE 8-continued

Levodopa plasma concentration

| Parameter | Pig 1 | Pig 2 | Pig 3 | Pig 4 | Mean (SEM) |
|---|---|---|---|---|---|
| AUC (µg · h/mL) | 20.6 | 22.1 | 9.56 | 13.4 | 16.4 (2.97) |
| $t_{1/2}$ (h) | 1.2 | 1.0 | 0.9 | 1.0 | 1.0 |

TABLE 9

Carbidopa plasma concentration

| Parameter | Pig 1 | Pig 2 | Pig 3 | Pig 4 | Mean (SEM) | |
|---|---|---|---|---|---|---|
| $C_{max}$ (ng/mL) | 92 | 132 | 20 | 17 | 65 (28) | LC gel |
| $T_{max}$ (h) | 0.5 | 0.5 | 0.5 | 0.5 | 0.5 (0) | |
| AUC (ng · h/mL) | 374 | 348 | 18 | 23 | 191 (99) | |
| $C_{max}$ (ng/mL) | 192 | 151 | 40 | 36 | 105 (39) | HC gel |
| $T_{max}$ (h) | 0.5 | 0.5 | 0.5 | 0.5 | 0.5 (0) | |
| AUC (ng · h/mL) | 751 | 393 | 41 | 47 | 308 (169) | |
| $C_{max}$ (ng/mL) | 204 | 369 | 28 | 32 | 158 (81) | Carbopol |
| $T_{max}$ (h) | 0.5 | 0.5 | 1.0 | 0.5 | 0.63 (0.13) | |
| AUC (ng · h/mL) | 578 | 660 | 36 | 38 | 328 (169) | |

Example 4

Further Bioavailability Studies in Human Subjects

Figure 4:
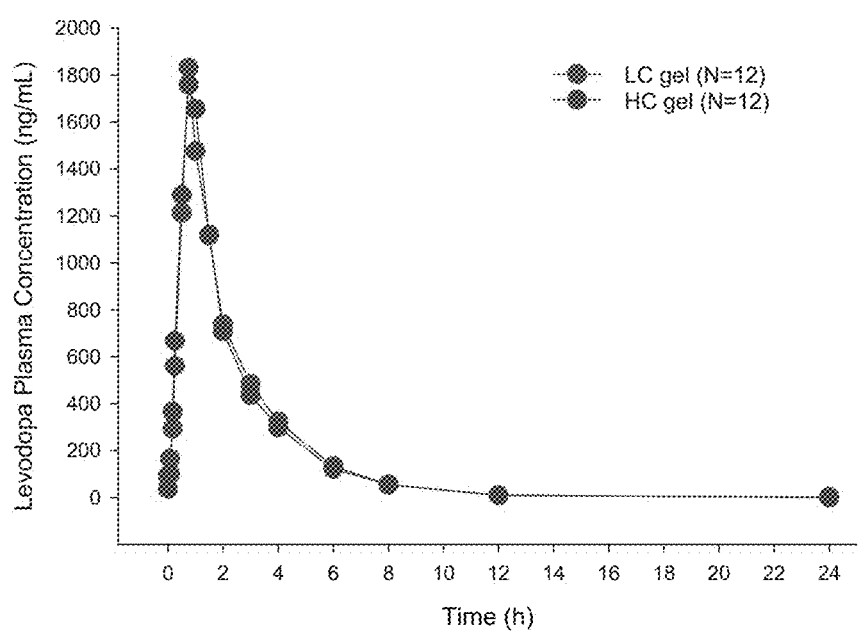
FIG. 4 shows average levodopa plasma concentrations in 12 human subjects at various time points post administration.
Figure 5:
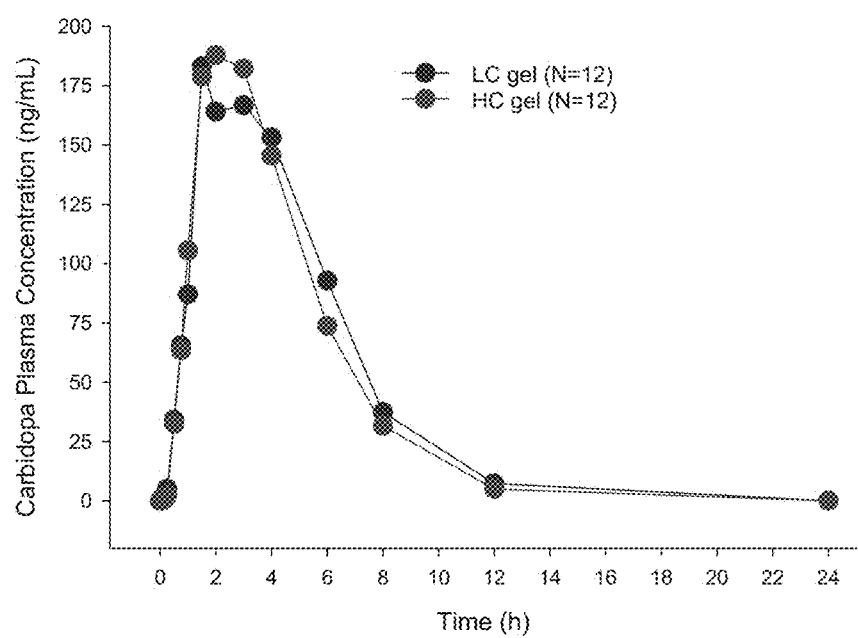
FIG. 5 shows average carbidopa plasma concentrations in 12 human subjects at various time points post administration.

To further test the bioavailability of the LC and HC formulations discussed in Example 3 above, a total of 12 subjects participated in an open label, single dose, randomized crossover study to test the bioavailability of the LC and HC formulations. Each subject received a single dose of levodopa (200 mg) and carbidopa monohydrate (50 mg) on the mornings of Day 1 and Day 4 under fasting conditions. Subjects were randomly assigned in equal numbers to the two sequences of commercially prepared LC formulation of and commercially prepared HC formulation. Each dose was administered over a 30 minute period via nasojejunal tube connected to a portable infusion pump. Patients receiving the LC formulation received a 10.0 mL dose. Patients receiving the HC formulation received a 5.0 mL dose, so that equal amounts of drug were delivered regardless of whether LC or HC formulation was administered. Subjects were confined for approximately 6 days (Check-in Day to Day 5). Serial blood samples for levodopa, carbidopa, and 3-O-methyldopa assays were collected after dosing on Day 1 and Day 4. Times for collection include 0 hour (prior to dose), at 5, 10, 15, 30, 45 minutes after the start of infusion, and at 1, 1.5, 2, 3, 4, 6, 8, 12, and 24 hours after the start of infusion. Bioavailability for levodopa is summarized in Table 10 below and in FIG. 4.

TABLE 10

Levodopa plasma concentration from test subjects (N = 12)

| Pharmacokinetic Parameters | 200 mg Levodopa in LC gel (% CV) | 200 mg Levodopa in HC gel (% CV) |
|---|---|---|
| $C_{max}$ (ng/mL) | 2100 (35) | 2100 (25) |
| $T_{max}$ (h) | 0.85 (18) | 0.81 (33) |
| $AUC_t$ (ng · h/mL) | 4000 (18) | 3930 (21) |
| $AUC_\infty$ (ng · h/mL) | 4080 (17) | 4010 (20) |
| $t_{1/2}^a$ (h) | 1.69 (12) | 1.85 (32) |

TABLE 11

Carbidopa plasma concentration from test subjects (N = 12)

| Pharmacokinetic Parameters | 50 mg Carbidopa in LC gel (% CV) | 50 mg Carbidopa in HC gel (% CV) |
|---|---|---|
| $C_{max}$ (ng/mL) | 242 (79) | 220 (45) |
| $T_{max}$ (h) | 3.0 (31) | 2.5 (42) |
| $AUC_t$ (ng · h/mL) | 956 (35) | 910 (45) |
| $AUC_\infty$ (ng · h/mL) | 1100 (30) | 1070 (39) |
| $t_{1/2}^a$ (h) | 1.82 (14) | 1.76 (18) |

These tests show that the HC formulation was equal to the LC formulation for levodopa $C_{max}$, $AUC_t$ and $AUC_\infty$ and for carbidopa $AUC_t$ and $AUC_\infty$. The 90% confidence interval for equal carbidopa $C_{max}$ is slightly beyond the 0.8 to 1.25 range. However, this is not a clinically relevant factor because dosing for efficacy is determined by the levodopa content, and not carbidopa. Studies show that peripheral dopa decarboxylase is saturated by carbidopa at approximately 70-100 mg a day, and advanced Parkinson's disease patients on levodopa/carbidopa gel treatment would surpass these daily carbidopa doses for saturation. The relative bioavailability of the LC and HC formulations for levodopa and carbidopa are summarized in Table 12 below.

TABLE 12

Bioequivalency of LC and HC gel formulations

| | Central value | | Relative bioavailability | | |
|---|---|---|---|---|---|
| Parameter | HC | LC | Point estimate | 90% Confidence | |
| $C_{max}$ (ng/mL) | 2040 | 1980 | 1.028 | (0.859, 1.231) | Levodopa |
| $AUC_t$ (ng · h/mL) | 3860 | 3890 | 0.991 | (0.922, 1.065) | |
| $AUC_\infty$ (ng · h/mL) | 3940 | 3970 | 0.993 | (0.926, 1.065) | |
| $C_{max}$ (ng/mL) | 198 | 205 | 0.963 | (0.739, 1.253) | carbidopa |
| $AUC_t$ (ng · h/mL) | 835 | 903 | 0.925 | (0.831, 1.029) | |
| $AUC_\infty$ (ng · h/mL) | 887 | 965 | 0.919 | (0.824, 1.025) | |

In summary, the amount of drug delivered was similar for both formulations. Doses delivered for both formulations were similar (~6% difference). Levodopa and carbidopa exposures were very similar for both formulations. Levodopa exposure variability was low to moderate (17-35% CV) for both the LC and HC formulations. Both the LC and HC formulations were equivalent for levodopa. The LC and HC formulations were equivalent for carbidopa except for the $C_{max}$ which is not clinically significant.

Figure 6:
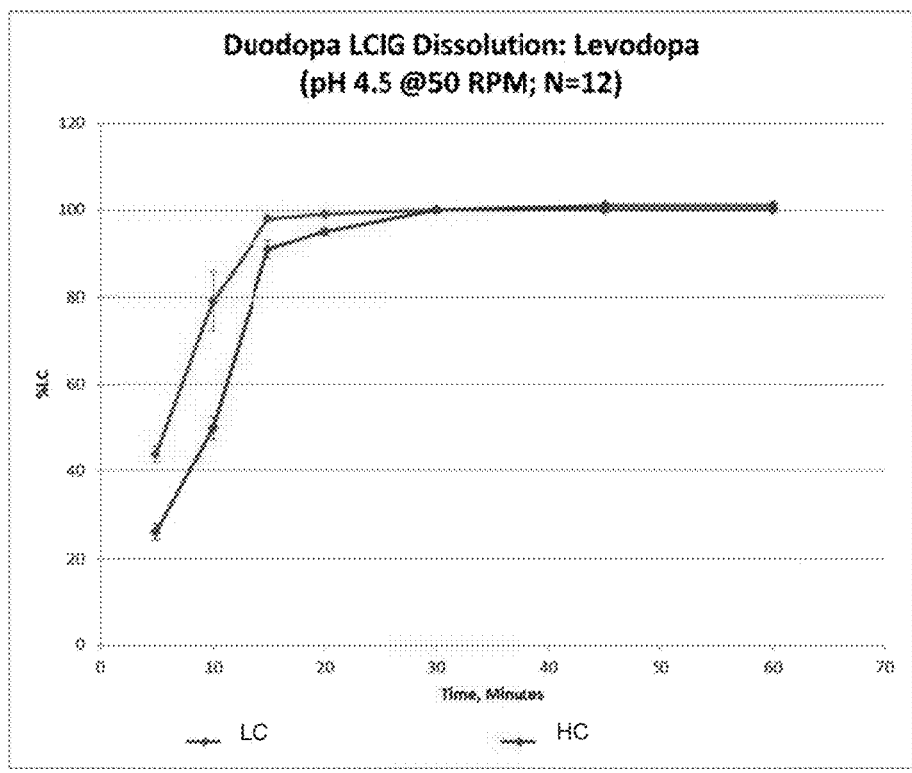
FIG. 6 shows the dissolution rate at which levodopa and carbidopa dissolve in a pH 4.5 media.
Figure 6:
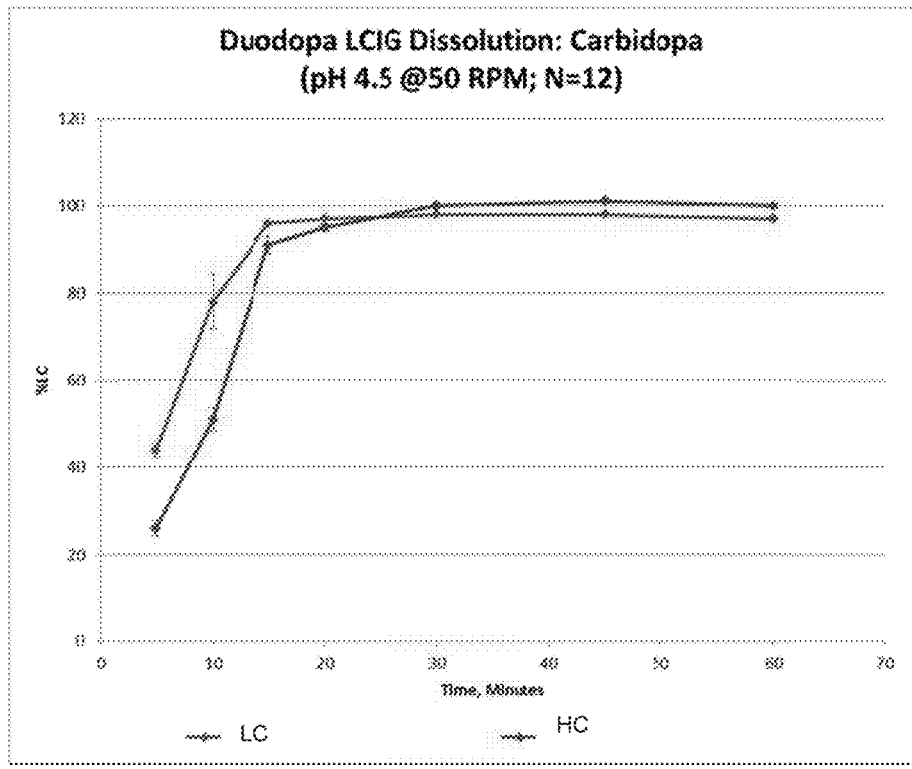
Figure 7:
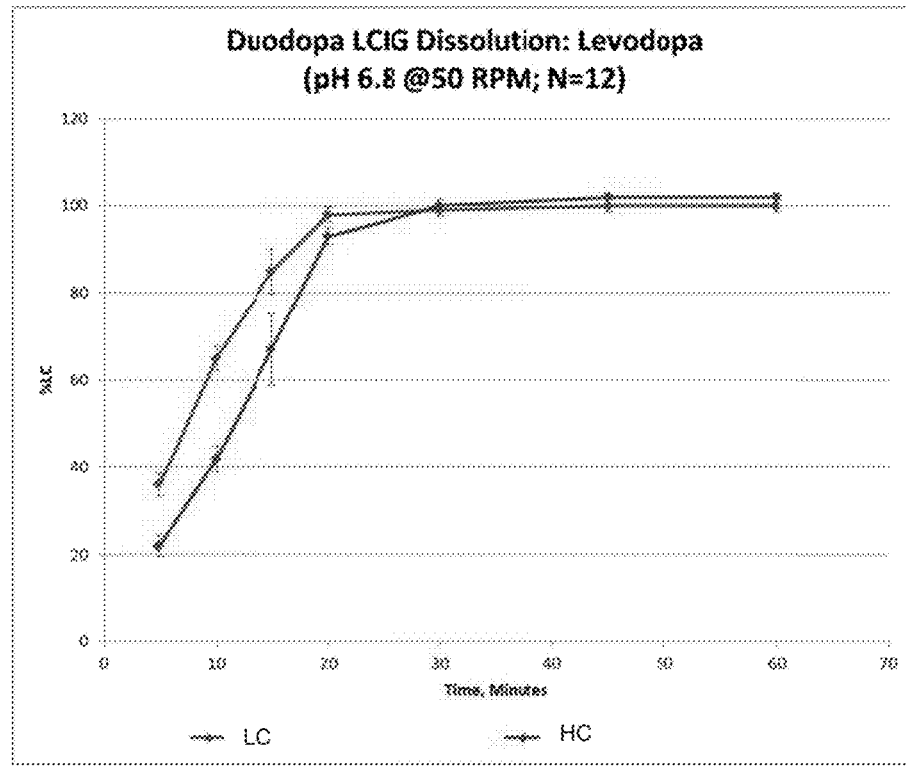
FIG. 7 shows the dissolution rate at which levodopa and carbidopa dissolve in a pH 6.8 media.
Figure 7:
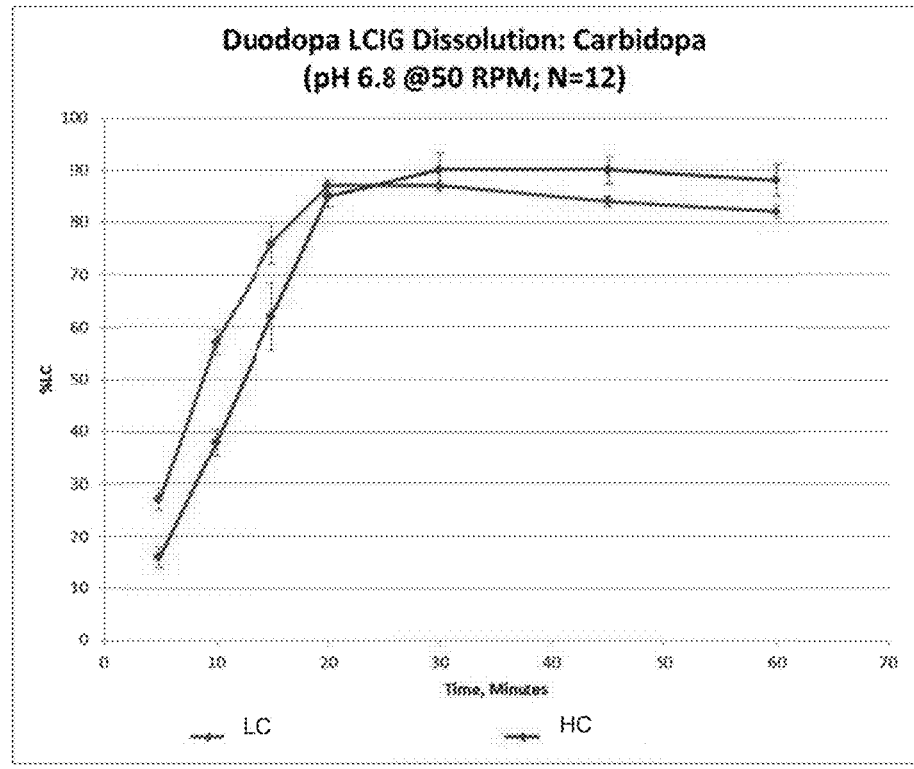

FIGS. 6 & 7 show that the LC and HC formulations have similar dissolution rates at pH 4.5 and 6.8, which supports the bioequivalency results summarized above. These dissolution trials were conducted by adding equal doses of drug formulations to beakers containing 500 mL of 50 mM sodium acetate buffer at pH 4.5 (±0.05) or pH 6.8 (±0.05). Each sample was maintained at 37° C. with agitation at 50 RPM during the procedure. Samples were drawn at 5, 10, 15, 20, 30, 45, and 60 minutes post addition of drug. The concentration of drug dissolved in the samples was measured by HPLC on a PHENOMENEX KINETEX C8 column (100×4.6 mm, 5 µm with SecurityGuard Cartridge) at 30° C. The mobile phase was 88:12 10 mM sodium heptane sulfonic acid (HAS) in 0.2% $H_3PO_4$:acetonitrile. The sample was eluted through the column at a rate of ~3.0 mL/min and measured by UV spectrophotometry ($OD_{280}$).

Example 5

Sedimentation and Storage Stability

Stokes' Law can be used to assess particle sedimentation and thus the physical stability of the HC formulation. Stokes' Law considers three forces acting on a particle situated in a continuous viscous fluid: buoyancy force, drag force, and gravitational force. When the forces are balanced and there is no net acceleration, the particle reaches a terminal or settling velocity given by:

$$v = (d^2(\rho_1 - \rho_2)g)/18\eta = (2r^2(\rho_1 - \rho_2)g)/9\eta$$

where v is the settling velocity; d is the particle diameter and r is the particle radius; $\rho_1$ is the density of the dispersed phase and $\rho_2$ is the density of the dispersion medium; g is the gravity constant; $\eta$ is the viscosity of the fluid at rest.

There are two factors that can be controlled in the HC formulation to modulate physical stability: particle size of levodopa and carbidopa monohydrate and viscosity of the gel-suspension. Levodopa and carbidopa monohydrate particle sizes are well controlled by the micronization process within the particle size limits mentioned herein. However, the viscosity can be adjusted by modifying the ratio of carmellose sodium viscosity grades. The viscosity of the fluid at rest is approximated by the low shear viscosity method. The minimum low shear viscosity necessary to achieve the desired physical stability is 44,590 cps based on this example, as shown in Tables 13 and 14.

them for levodopa and carbidopa content using a high pressure liquid chromatography (HPLC) system with guard column: Agilent, Zorbax Eclipse XDB-C8, 4.6×12.5 mm, 5 μm (Agilent, part number 820950-926) with Agilent Hardware kit High Press, (Agilent, Part number 820999-901) or equivalent; and analytical column: Zorbax Eclipse XDB-C8, 150×4.6 mm, 5 μm (Agilent part no. 993967-906). The chromatographic conditions are shown in Table 15.

TABLE 15

Chromatographic Conditions for Levodopa/Carbidopa Concentration Test

| | |
|---|---|
| Flow Rate | ~1.2 mL/min. |
| Injection Volume | 5 μL |
| Autosampler Temp. | 5° C. |
| Column Temp. | ~30° C. |
| Sample Diluent | 0.1M phosphoric acid in water |
| Mobile phase A | 10 mM sodium heptane sulfonic acid in 0.2% phosphoric acid |
| Mobile phase B | Acetonitrile |

| | Time (min.) | % Mobile phase A | % Mobile phase B |
|---|---|---|---|
| Isocratic Profile | 0 | 88 | 12 |
| Run Time | Approximately 12 to 15 minutes | | |

TABLE 13

Acceptance Values for Levodopa

| | | Lot 1 | Lot 2 | Lot 3 | Lot 4 | Lot 5 | Lot 6 |
|---|---|---|---|---|---|---|---|
| Interval Release | LS Viscosity (cps) | 32,393 | 36,692 | 39,692 | 44,590 | 45,590 | 45,790 |
| | AV | 4.9 | 5.0 | 6.1 | 4.1 | 3.7 | 3.9 |
| 15 weeks at 5° C. | AV | 26.1 | 31.2 | 20.6 | 4.7 | 2.8 | 3.1 |
| | Result | Fail | Fail | Fail | Pass | Pass | Pass |

TABLE 14

Acceptance Values for Carbidopa

| | | Lot 1 | Lot 2 | Lot 3 | Lot 4 | Lot 5 | Lot 6 |
|---|---|---|---|---|---|---|---|
| Interval Release | LS Viscosity (cps) | 32,393 | 36,692 | 39,692 | 44,590 | 45,590 | 45,790 |
| | AV | 3.6 | 4.7 | 3.8 | 5.2 | 5.3 | 4.4 |
| 15 weeks at 5° C. | AV | 10 | 8.4 | 6.4 | 0.7 | 1.8 | 1.9 |
| | Result | Fail | Fail | Fail | Pass | Pass | Pass |

The criterion for "acceptable" physically stable was the absence of significant sedimentation for at least 15 weeks under refrigerated storage conditions (e.g., 5° C.). The physical stability was assessed by drawing 5 ml samples from the DDR for a total of 10 samples and then analyzing A sample was defined as physically stable if the Acceptance Value (AV), defined by Equation 2, was no more than 15 for both levodopa and carbidopa.

$$AV = |M - \bar{X}| + ks \qquad \text{Equation 2.}$$

The definition of each variable in Equation 2 is shown in Table 16.

TABLE 16

Definition of Variables Used in Calculating the Acceptance Value

| Variable | Definition | Conditions | Value |
|---|---|---|---|
| $\bar{X}$ | Mean of individual contents ($X_1$, $X_2$, ..., $X_n$), expressed as a percentage of the label claim | | |

TABLE 16-continued

Definition of Variables Used in Calculating the Acceptance Value

| Variable | Definition | Conditions | Value |
|---|---|---|---|
| $X_1, X_2, \ldots, X_n$ | Individual contents of the units tested, expressed as a percentage of the label claim | | |
| n | Sample size (# of units in sample) | | |
| k | Acceptability constant | If n = 10, | then k = 2.4 |
| | | If n = 30, | then k = 2.0 |
| s | Sample standard deviation | | $\left[\dfrac{\sum_{i=1}^{n}(x_i - \overline{X})^2}{n-1}\right]^{\frac{1}{2}}$ |
| RSD | Relative standard deviation (the sample standard deviation expressed as a percentage of the mean) | | $100s/\overline{X}$ |
| M (case 1) | Reference value to be applied where T ≤ 101.5 | If 98.5% ≤ $\overline{X}$ ≤ 101.5% | M = $\overline{X}$ (AV = ks) |
| | | If $\overline{X}$ < 98.5% | M = 98.5% (AV = 98.5 − $\overline{X}$ + ks) |
| | | If $\overline{X}$ > 101.5% | M = 101.5% (AV = $\overline{X}$ − 101.5 + ks) |
| M (case 2) | Reference value to be applied where T > 101.5 | If 98.5 ≤ $\overline{X}$ ≤ T | M = $\overline{X}$ (AV = ks) |
| | | If $\overline{X}$ < 98.5% | M = 98.5% (AV = 98.5 − $\overline{X}$ + ks) |
| | | If $\overline{X}$ > T | M = T % (AV = $\overline{X}$ − T + ks) |

Example 6

Effect of Oxygen

Figure 11:
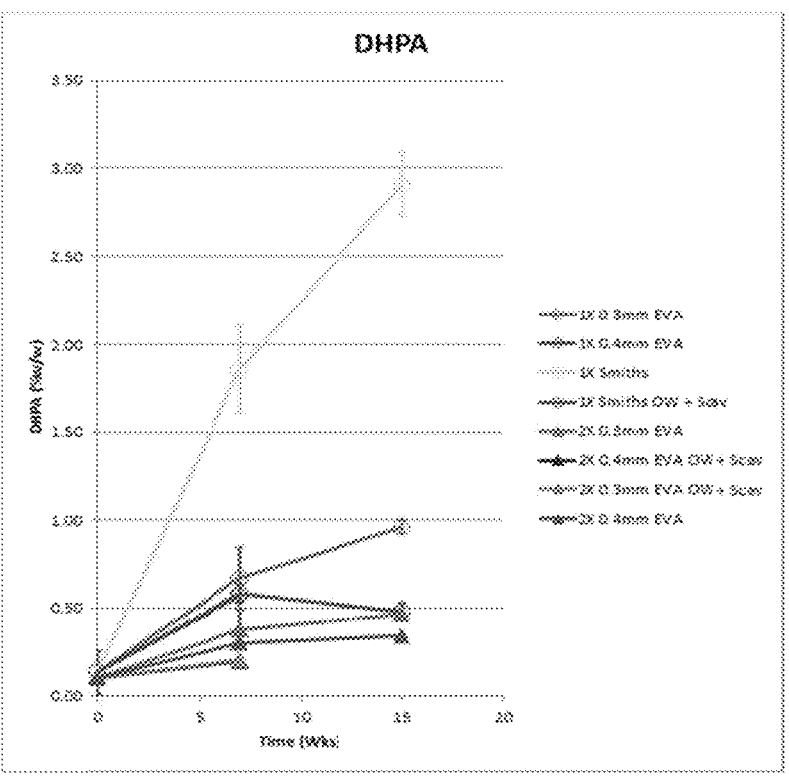
FIG. 11 shows the effects of oxygen scavengers in different packages on the accumulation of DHPA (panel A) and DHPPA (panel B) degradation products. The abbreviations in the legend have the following significations: 1×=2 w/w % levodopa, 0.5 w/w % carbidopa; 2×=4 w/w % levodopa, 1.0 w/w % carbidopa; EVA=container closure bag made from EVA/EVOH/EVA material; Smiths=PVC bag used in Smiths Medical cassette reservoir; OW+Scav=with oxygen scavenger inside overwrapped aluminum foil pouch.
Figure 11:
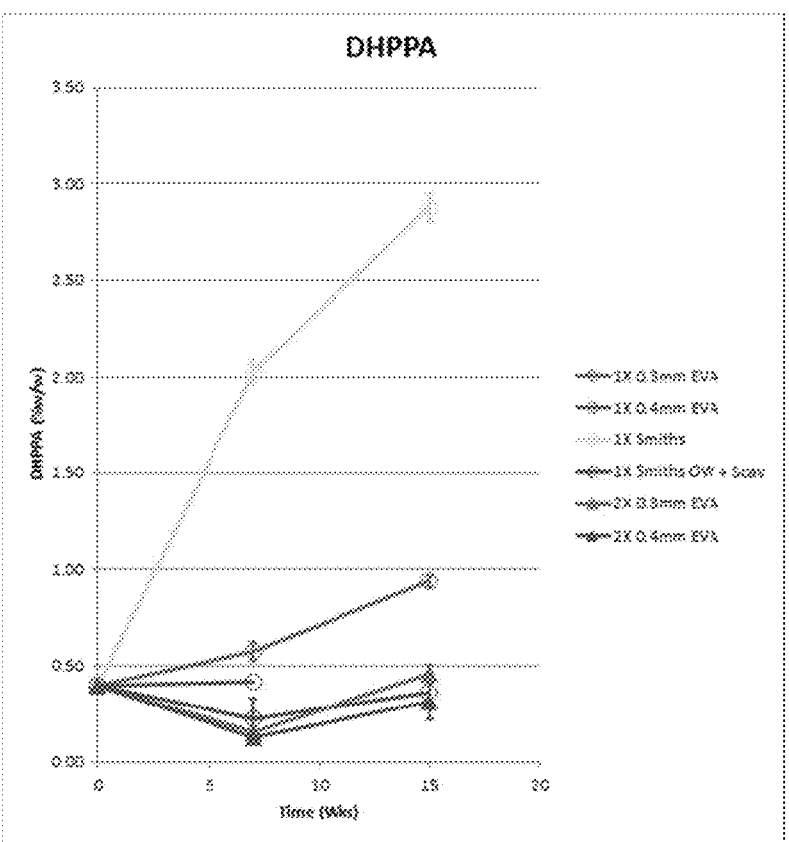

The high concentration formulation can be purged of oxygen during manufacturing and stored in containers with low oxygen permeation. This significantly decreases the rate of degradation compared to a formulation manufactured and stored in ambient oxygen conditions. Depending on the packaging, the disposable drug reservoirs can have very low oxygen content at the time of filling. These DDRs consist of a hard shell outer, an inner package, and tubings/connectors. The inner bag serves to maintain the $O_2$ content of the final drug product gel. The EVA/EVOH/EVA bag has a very low $O_2$ permeability (oxygen transmission rate for the EVA/EVOH/EVA sheet film was approximately 0.95 cc/(100 in$^2$*day). FIG. 11 charts the accumulation of DHPA breakdown product when LC and HC gel formulations are left for 15 weeks 0.3 mm thick EVA/EVOH/EVA bags at 2-8° C. Moreover, $N_2$ sparging can be used in the manufacture process to purge oxygen. The combination of $N_2$ sparging and low $O_2$ permeability EVA/EVOH/EVA bag ensures a very low overall $O_2$ content.

Figure 8:
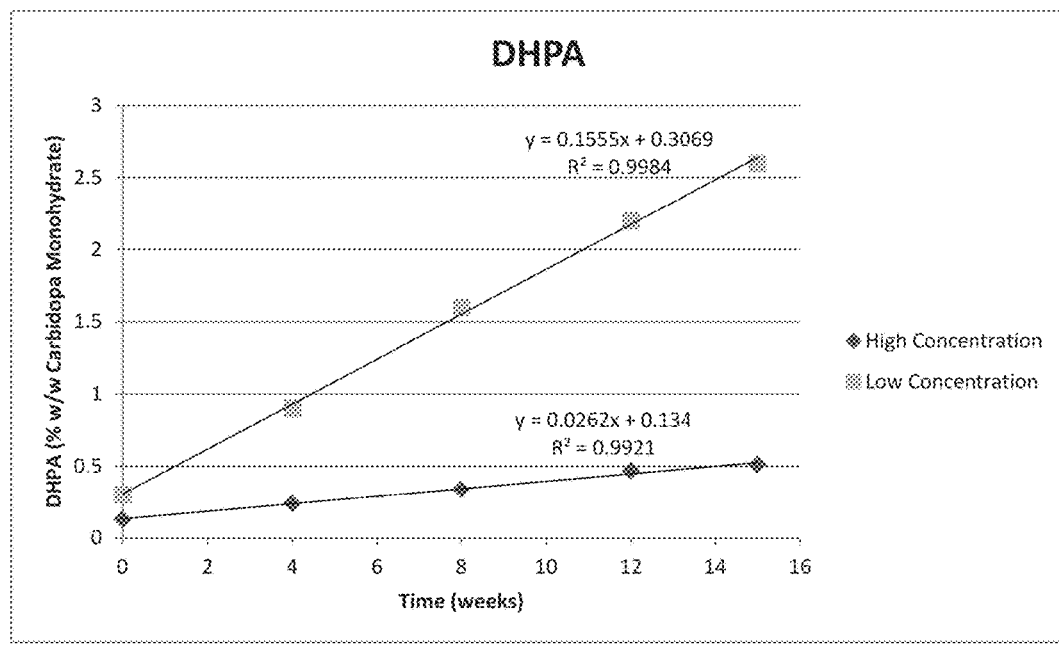
FIG. 8 charts the decomposition of low and high concentration gel formulations into 3,4-dihydroxyphenylacetone (DHPA) over the course of 15 weeks storage at 2-8° C.
Figure 9:
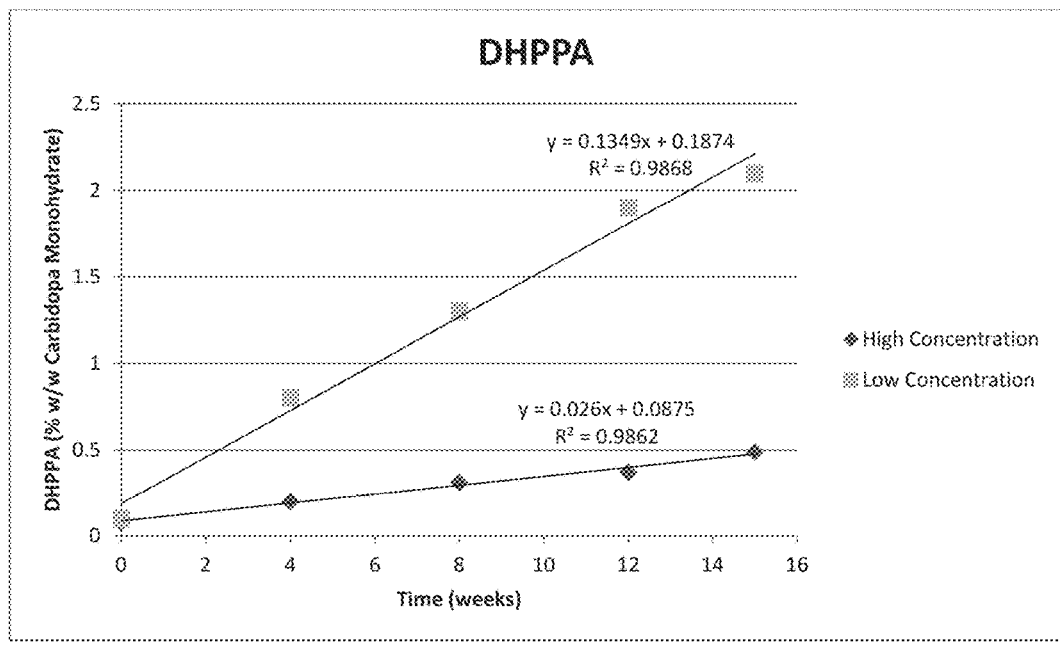
FIG. 9 charts the decomposition of low and high concentration gel formulations into 2-methyl-3-(3,4-dihydroxyphenyl) propanoic acid (DHPPA) over the course of 15 weeks storage at 2-8° C.
Figure 10:
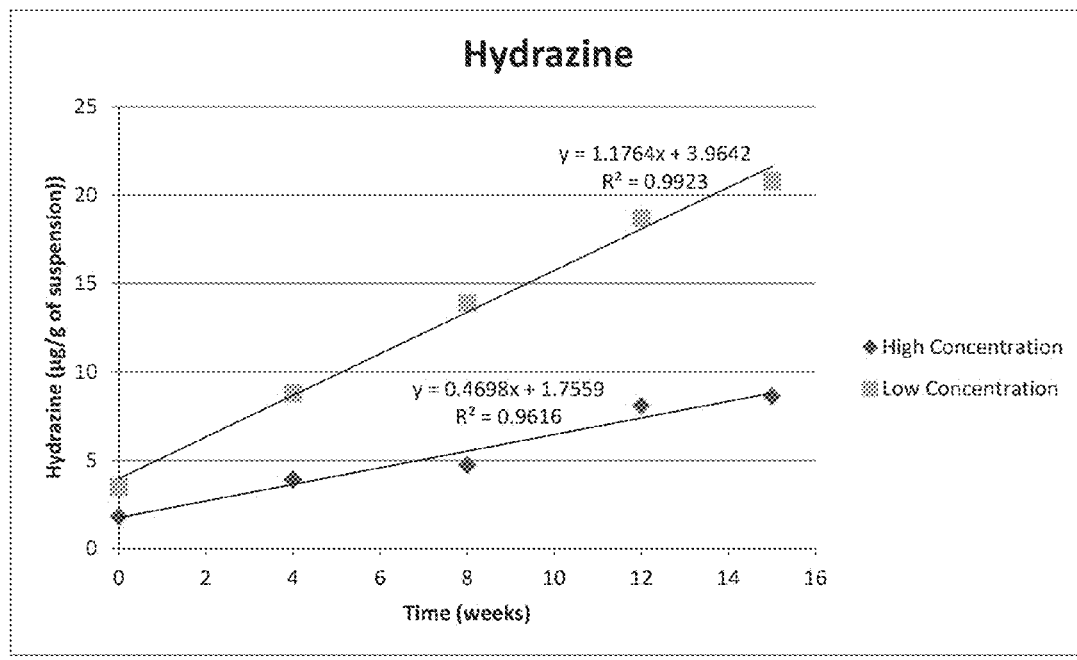
FIG. 10 charts the decomposition of low and high concentration gel formulations into hydrazine over the course of 15 weeks storage at 2-8° C.

To test the effects of this low $O_2$ packaging, samples of LC gel formulation were not sparged with $N_2$ and were packaged in polyvinyl chloride (PVC) bags. Samples of HC gel formulation were sparged with $N_2$ and packaged in EVA/EVOH/EVA bags. Both sets of bags were monitored for the development of DHPA, DHPPA, and hydrazine degradation products over time. The results of these tests are shown in FIGS. 8-10 below. DHPA and DHPPA were analyzed using HPLC system with analytical column: Waters, X-Bridge, C8, 3.5 μm particles, 4.6×150 mm column (catalogue 186003055) or equivalent with a stationary phase of octylsilane chemically bonded to totally porous silica particles (USP L7); and guard column: Phenomenex Security Guard Cartridge PFP 4×3.0 mm (catalogue AJ0-4290) or equivalent, security guard cartridge holder, Phenomenox, (catalogue AJ0-6071) or equivalent. HPLC settings for the DHPA and DHPPA tests are shown in Table 17 below.

TABLE 17

Chromatographic Conditions for DHPA/DHPPA Test

| | |
|---|---|
| Wavelength | 220 nm |
| Flow Rate | 1.3 ± 0.2 mL/min |
| Injection Volume | 20 μL |
| Autosampler Temp. | 8 ± 2° C. |
| Column Temp. | 30 ± 1° C. |
| Sample Diluent | 0.1M Phosphoric acid in water |
| Mobile phase A | 10% phosphate buffer, 10% 0.1M sodium heptane sulfonic acid and 80% water |
| Mobile phase B | 10% phosphate buffer, 10% 0.1M sodium heptane sulfonic acid, 20% Acetonitrile and 60% water |

| | Time (min.) | % Mobile phase A | % Mobile phase B |
|---|---|---|---|
| Gradient Profile | 0 | 85 | 15 |
| | 18.3 | 25 | 75 |
| | 19.0 | 25 | 75 |
| | 20.0* | 85 | 15 |
| | 27.0* | 85 | 15 |

*Gradient equilibration time

Hydrazine was analyzed using HPLC with a Grace Scientific column, Grom-Sil 120 ODS-5, 250×4.6 mm, 5 μm (Part No. GS0D50512S2505) or equivalent after the sample was eluted from SPE column: Chromabond® HR-X (15 mL/1000 mg) by Macherey-Nagel, Part No. 730941. HPLC settings for the hydrazine tests are shown in Table 18 below.

TABLE 18

Chromatographic Conditions for Hydrazine Test

| | |
|---|---|
| Wavelength | 313 nm |
| Flow Rate | 1.0 mL/min |

TABLE 18-continued

Chromatographic Conditions for Hydrazine Test

| | |
|---|---|
| injection Volume | 30 µL |
| Autosampler Temp. | 5° C. |
| Column Temp. | 40° C. |
| Sample Diluent | 50 mM sulfuric acid in water; 1% solution of benzaldehyde in methanol; 100 mM solution of sodium borate in water |
| Mobile phase A | Purified water |
| Mobile phase B | Acetonitrile |
| Isocratic Profile | 30% A, 70% B |
| Run Time | 18 minutes |

Degradation can also be slowed by adding oxygen scavengers (e.g. either ferrous or non-ferrous based, canister or sachet) and placing into a low $O_2$ permeability secondary container. The effects of oxygen scavengers in different packages on the accumulation of DHPA and DHPPA degradation products are illustrated in FIG. 11 below.

Although the invention has been described with respect to specific embodiments and examples, it should be appreciated that other embodiments utilize the concept of the present invention are possible without departing from the scope of the invention. The present invention is defined by the claimed elements, and any and all modifications, variations, or equivalents that fall within the true spirit and scope of the underlying principles.

VIII. Further Embodiments

Embodiment 1. A pharmaceutical composition comprising a levodopa active agent and a carbidopa active agent for intraduodenal administration wherein the levodopa active agent and the carbidopa active agent are suspended in an aqueous carrier, characterized in that the levodopa active agent and the carbidopa active agent in the carrier has a high shear viscosity of no more than about 4500 cps at room temperature and a low shear viscosity of no less than about 45000 cps under refrigerated conditions and a ratio of low shear viscosity to high shear viscosity of not less than 10.

Embodiment 2. The pharmaceutical composition according to Embodiment 1, wherein the pharmaceutical composition comprises: a levodopa active agent in an amount of about 4.0 weight/weight percent of the total composition; a carbidopa monohydrate active agent in an amount of about 1.0 weight/weight percent of the total composition; a liquid vehicle (e.g., in an amount of from about zero percent to about 95 weight/weight percent of the total composition and/or selected from the group consisting of water), and wherein the aqueous carrier comprises a suspending agent (e.g., one or more polymer-based suspending agent, such as an acrylic acid-based polymer or a polymer selected from the group consisting of hydroxypropylcellulose, hydroxymethylcellulose, and sodium carboxymethyl cellulose).

Embodiment 3. The pharmaceutical composition according to Embodiment 1 or 2, wherein the pharmaceutical composition does not experience degradation into DHPA at a rate faster than 0.04 w/w % per week.

Embodiment 4. The pharmaceutical composition according to any one of the previous Embodiments, wherein the pharmaceutical composition does not experience degradation into DHPPA at a rate faster than 0.04 w/w % per week.

Embodiment 5. The pharmaceutical composition according to any one of the previous Embodiments, wherein the pharmaceutical composition does not experience degradation producing hydrazine at a rate faster than 0.6 µg/g per week.

Embodiment 6. The pharmaceutical composition according to any one of the previous Embodiments, wherein the pharmaceutical composition is present in a lower $O_2$ permeable primary or secondary container.

Embodiment 7. A pharmaceutical dosage form comprising the pharmaceutical composition of any one of the previous Embodiments in a disposable drug reservoir having an oxygen impermeable enclosure disposed therein, wherein the oxygen impermeable enclosure is purged with an inert gas and an oxygen scavenger is added, and optionally, wherein the pharmaceutical dosage form is suitable for use in a continuous infusion pump capable of delivering the composition in a therapeutically effective manner.

Embodiment 8. A method of preparing the pharmaceutical composition according to any one of Embodiments 1-6, wherein the method comprises: adding a levodopa active agent and a carbidopa active agent to water to form a slurry; adding the slurry to one or more suspending agents (e.g., an acrylic acid-based polymer or a polymer selected from the group consisting of hydroxypropylcellulose, hydroxymethylcellulose, and sodium carboxymethyl cellulose) to form a suspension; subjecting the suspension to $N_2$ sparging; and optionally, loading the suspension into a lower oxygen permeability container.

Embodiment 9. The method according to Embodiment 8, wherein, prior to forming the suspension, the levodopa active agent has a particle size distribution of: (i) D50 less than or equal to about 5 µm; (ii) D90 less than or equal to about 11 µm; and (iii) D100 less than or equal to about 22 µm; and the carbidopa active agent has a particle size distribution of: (i) D50 less than or equal to about 3 µm; (ii) D90 less than or equal to about 7 µm; and (iii) D100 less than or equal to about 21 µm.

Embodiment 10. The pharmaceutical composition according to any one of Embodiments 1-6 prepared by: adding a levodopa active agent and a carbidopa active agent to water to form a slurry; adding the slurry to one or more suspending agents (e.g., an acrylic acid-based polymer or a polymer selected from the group consisting of hydroxypropylcellulose, hydroxymethylcellulose, and sodium carboxymethyl cellulose) to form a suspension; subjecting the suspension to $N_2$ sparging; and optionally, loading the suspension into a lower oxygen permeability container.

Embodiment 11. The pharmaceutical composition according to Embodiment 10, wherein, prior to forming the suspension, the levodopa active agent has a particle size distribution of: (i) D50 less than or equal to about 5 µm; (ii) D90 less than or equal to about 11 µm; and (iii) D100 less than or equal to about 22 µm; and the carbidopa active agent has a particle size distribution of: (i) D50 less than or equal to about 3 µm; (ii) D90 less than or equal to about 7 µm; and (iii) D100 less than or equal to about 21 µm.

Embodiment 12. A method of treating Parkinson's disease in a patient in need thereof, wherein the method comprises administering to the patient a pharmaceutical composition comprising a levodopa active agent and a carbidopa active agent for intraduodenal administration, wherein the levodopa active agent and carbidopa active agent are provided in a therapeutically effective manner for the patient and, suspended in an aqueous carrier, characterized in that the levodopa active agent and the carbidopa active agent in the carrier has a high shear viscosity of no more than about 4500 cps at room temperature and a low shear viscosity of no less than about 45000 cps under refrigerated conditions and a ratio of low shear viscosity to high shear viscosity of not less than 10 and optionally, wherein the pharmaceutical composition is administered in a pharmaceutical dosage form according to Embodiment 7.

Embodiment 13. The method according to Embodiment 12, wherein the method comprises substantially continuous administration of the pharmaceutical composition for a period of at least about 16 hours or for a period of at least about 24 hours.

Embodiment 14. The method according to Embodiment 12 or 13, wherein the pharmaceutical composition comprises: a levodopa active agent in an amount of about 4.0 weight/weight percent of the total composition; and a carbidopa monohydrate active agent in an amount of about 1.0 weight/weight percent of the total composition.

Embodiment 15. The method according to any one of Embodiments 12-14, wherein the aqueous carrier comprises one or more polymer-based suspending agent (e.g., an acrylic acid-based polymer or a polymer selected from the group consisting of hydroxypropylcellulose, hydroxymethylcellulose, and sodium carboxymethyl cellulose).

Embodiment 16. A kit comprising the pharmaceutical composition of any one of Embodiments 1-6 or the pharmaceutical dosage form of Embodiment 7.

What is claimed is:

1. A pharmaceutical composition for intraduodenal administration comprising:
    (a) a levodopa active agent in an amount of about 4.0 weight/weight percent of the total composition;
    (b) a carbidopa monohydrate active agent in an amount of about 1.0 weight/weight percent of the total composition;
    (c) one or more polymer-based suspending agents selected from the group consisting of hydroxypropylcellulose, hydroxymethylcellulose, and sodium carboxymethyl cellulose; and
    (d) water,
    wherein the pharmaceutical composition has:
    (i) a high shear viscosity of no more than about 4500 cps at 22° C. and 24.1 $s^{-1}$;
    (ii) a low shear viscosity of no less than about 45000 cps at 5° C. and 1 $s^{-1}$; and
    (iii) a ratio of low shear viscosity to high shear viscosity of not less than 10.

2. The pharmaceutical composition according to claim 1, wherein the one or more polymer-based suspending agents is sodium carboxymethyl cellulose.

3. The pharmaceutical composition according to claim 2, wherein the concentration of water is in an amount of from about zero percent to about 95 weight/weight percent of the total composition.

4. The pharmaceutical composition according to claim 3, wherein the pharmaceutical composition does not experience degradation into DHPA at a rate faster than 0.06 w/w% per week.

5. The pharmaceutical composition according to claim 3, wherein the pharmaceutical composition does not experience degradation into DHPPA at a rate faster than 0.06 w/w% per week.

6. The pharmaceutical composition according to claim 3, wherein the pharmaceutical composition does not experience degradation producing hydrazine at a rate faster than 0.75 μg/g per week.

7. The pharmaceutical composition according to claim 3, wherein the pharmaceutical composition is present in a lower $O_2$ permeable primary or secondary container.

8. A pharmaceutical dosage form comprising the pharmaceutical composition of claim 1 in a disposable drug reservoir having an oxygen impermeable enclosure disposed therein, wherein the oxygen impermeable enclosure is purged with an inert gas and an oxygen scavenger is added.

9. The pharmaceutical dosage form according to claim 8, wherein the pharmaceutical dosage form is suitable for use in a continuous infusion pump capable of delivering the composition in a therapeutically effective manner.

10. A kit comprising the pharmaceutical composition of claim 1.

11. A kit comprising the pharmaceutical dosage form of claim 8.

* * * * *

UNITED STATES PATENT AND TRADEMARK OFFICE
CERTIFICATE OF CORRECTION

PATENT NO. : 10,117,843 B2
APPLICATION NO. : 15/001392
DATED : November 6, 2018
INVENTOR(S) : Rajkumar Conjeevaram et al.

It is certified that error appears in the above-identified patent and that said Letters Patent is hereby corrected as shown below:

In the Claims

Claim 1, Column 29, Line 38: "at 5° C. and 1...." should read "at 5° C. and 0.1..."

Signed and Sealed this
Twelfth Day of December, 2023

Katherine Kelly Vidal
*Director of the United States Patent and Trademark Office*